United States Patent
Huh

(10) Patent No.: US 11,365,450 B2
(45) Date of Patent: Jun. 21, 2022

(54) GROUP CLASSIFICATION AND PROGNOSIS PREDICTION SYSTEM BASED ON BIOLOGICAL CHARACTERISTICS OF GASTRIC CANCER

(71) Applicant: Novomics Co., Ltd., Seoul (KR)

(72) Inventor: Yong Min Huh, Seoul (KR)

(73) Assignee: Novomics Co., Ltd., Seoul (KR)

( * ) Notice: Subject to any disclaimer, the term of this patent is extended or adjusted under 35 U.S.C. 154(b) by 298 days.

(21) Appl. No.: 16/341,931

(22) PCT Filed: Apr. 24, 2018

(86) PCT No.: PCT/KR2018/004732
§ 371 (c)(1),
(2) Date: Apr. 15, 2019

(87) PCT Pub. No.: WO2018/199589
PCT Pub. Date: Nov. 1, 2018

(65) Prior Publication Data
US 2019/0241972 A1 Aug. 8, 2019

(30) Foreign Application Priority Data
Apr. 24, 2017 (KR) ........................ 10-2017-0052365

(51) Int. Cl.
| | |
|---|---|
| C12Q 1/6886 | (2018.01) |
| G16B 40/00 | (2019.01) |
| G16B 5/00 | (2019.01) |
| G16B 25/00 | (2019.01) |
| G16B 5/20 | (2019.01) |
| G16B 20/00 | (2019.01) |
| G16B 40/20 | (2019.01) |
| G16B 25/10 | (2019.01) |
| G16B 40/30 | (2019.01) |

(52) U.S. Cl.
CPC ............ *C12Q 1/6886* (2013.01); *G16B 5/00* (2019.02); *G16B 5/20* (2019.02); *G16B 25/00* (2019.02); *G16B 40/00* (2019.02); *C12Q 2600/118* (2013.01); *C12Q 2600/158* (2013.01); *G16B 20/00* (2019.02); *G16B 25/10* (2019.02); *G16B 40/20* (2019.02); *G16B 40/30* (2019.02)

(58) Field of Classification Search
None
See application file for complete search history.

(56) References Cited

U.S. PATENT DOCUMENTS

| | | |
|---|---|---|
| 2011/0059452 A1 | 3/2011 | Goldenring et al. |
| 2013/0337449 A1 | 12/2013 | Paik et al. |
| 2014/0287939 A1 | 9/2014 | Wu |

FOREIGN PATENT DOCUMENTS

| | | |
|---|---|---|
| EP | 2982986 | 2/2016 |
| KR | 10-2012-0065959 | 6/2012 |
| KR | 10-2014-0121523 | 10/2014 |
| WO | WO 2012/081898 | 6/2012 |
| WO | WO 2015/172201 | 11/2015 |

OTHER PUBLICATIONS

Chen (Atherclerosis 2013 vol. 226 pp. 149-152).*
Raitoharju et al. A comparison of the accuracy of Illumina HumanHT-12 v3 Expression BeadChip and TaqMan qRT-PCR gene expression results in patient samples from the Tampere Vascular Study Atherosclerosis vol. 226, pp. 149-152 (Year: 2013).*
VanGuilder et al. Twenty-five years of quantitative PCR for gene expression analysis BioTecnhniques vol. 44, pp. 619-626 (Year: 2008).*
Hippo et al. Global Gene Expression Analysis of Gastric Cancer by Oligonucleotide Microarrays Cancer Research vol. 62, pp. 233-240 (Year: 2002).*
Jiang et al. Gene expression profiling of gastric cancer European Review for Medical and Pharmacological Sciences vol. 18, pp. 2109-2115 (Year: 2014).*
Cui et al. Gene-Expression Signatures Can Distinguish Gastric Cancer Grades and Stages PLoS ONE vol. 6, article e17819 (Year: 2011).*
Marimuthu et al. Gene Expression Profiling of Gastric Cancer Journal of Proteomics and Bioinformatics vol. 4, pp. 74-82 (Year: 2011).*
International Search Report and the Written Opinion dated Jul. 26, 2018 From the International Searching Authority Re. Application No. PCT/KR2018/004732 and Its Translation of Search Report Into English. (10 Pages).
Tong et al. "Serum Biomarker Panels for Diagnosis of Gastric Cancer", OncoTargets and Therapy, 9: 2455-2463, Published Online Apr. 26, 2016.
Wang et al. "Identification of Specific Biomarkers for Gastric Adenocarcinoma by ITRAQ Proteomic Approach", Scientific Reports, 6: 38871-1-38871-15, Published Online Dec. 12, 2016.
Supplementary European Search Report and the European Search Opinion dated Jan. 13, 2021 From the European Patent Office Re. Application No. 18790388.5. (8 Pages).
Lee et al. "Development and Validation of A Six-Gene Recurrence Risk Score Assay for Gastric Cancer", Clinical Cancer Research, XP055677783, 22(24): 6228-6235, Published Online Sep. 21, 2016.
Tao et al. "CEP55 Contributes to Human Gastric Carcinoma by Regulating Cell Proliferation", Tumor Biology, XP036267384, 35(5): 4389-4399, Published Online Jan. 4, 2014.

* cited by examiner

Primary Examiner — John S Brusca

(57) ABSTRACT

The present invention relates to a group classification and prognosis prediction system based on the biological characteristics of gastric cancer, and an algorithm capable of predicting the prognosis of advanced gastric cancer in terms of overall survival by using a quantified value of an mRNA expression level of a target gene group has been developed and this may be used as auxiliary information for determining a treatment method of a gastric cancer patient.

4 Claims, 10 Drawing Sheets

Specification includes a Sequence Listing.

Fig. 2A
Fig. 2B
Fig. 2C
Fig. 2D
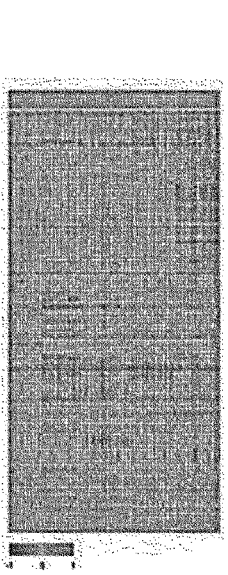
a GSE13861p
Inflammatory
Intestinal
Gastric
Mixed-stromal
Mesenchymal
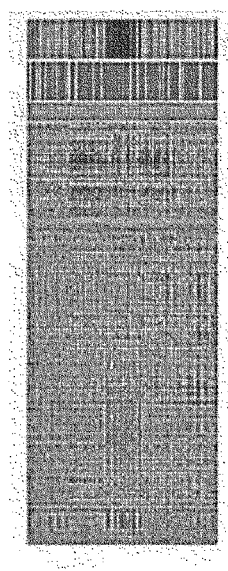
b GSE62254 (ACRG)
MSS/TP53-
MSS/TP53+
MSI
EMT
EBV-
EBV+
N/A
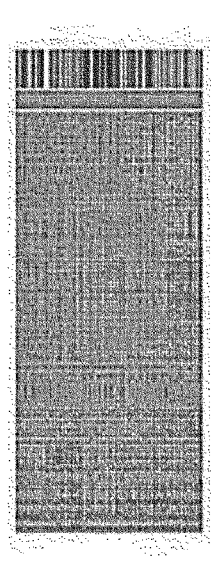
c TCGA
EBV
GS
CIN
MSI
N/A
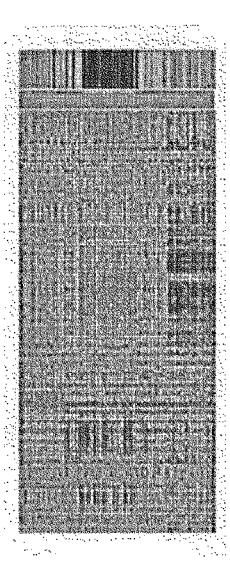
d GSE15459 (Singapore)
Invasive
Proliferative
Metabolic
Unstable

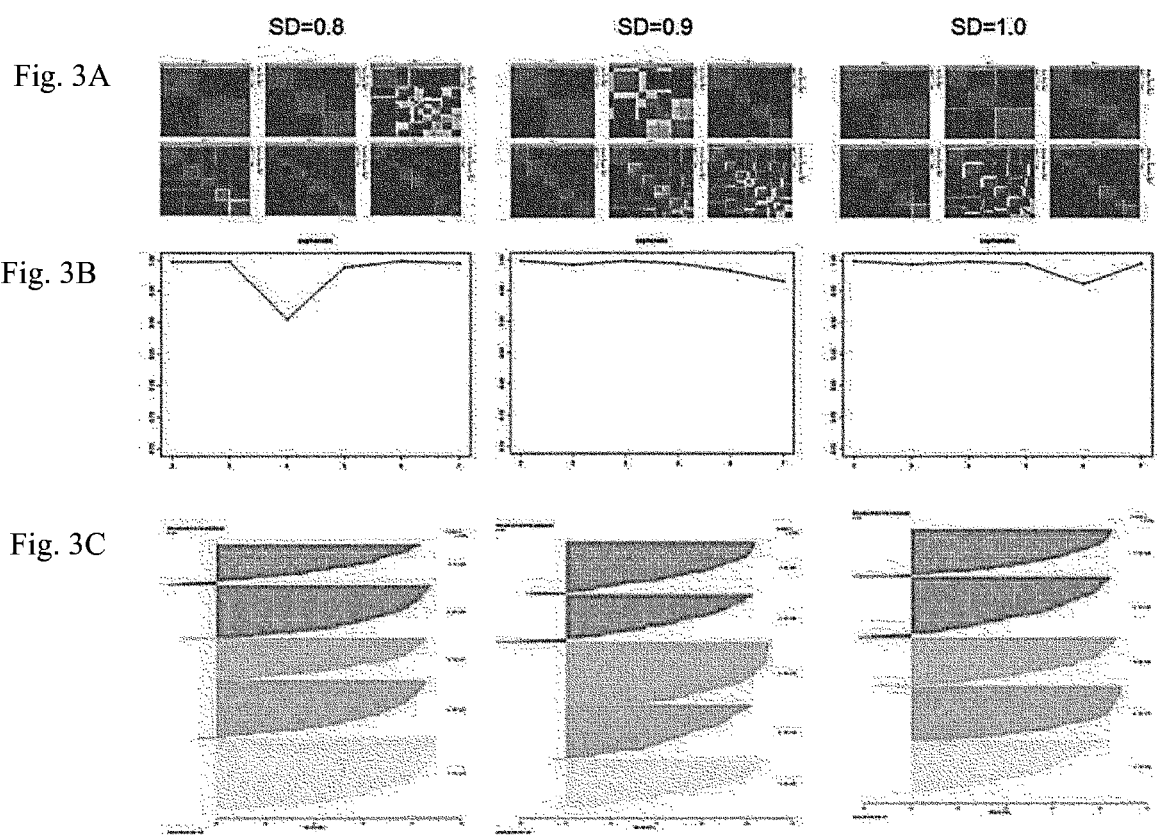

Fig. 4A
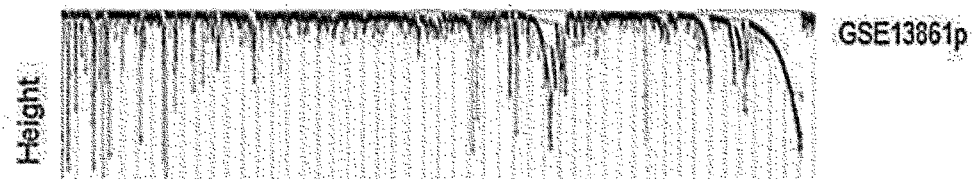
Fig. 4B
Fig. 4C
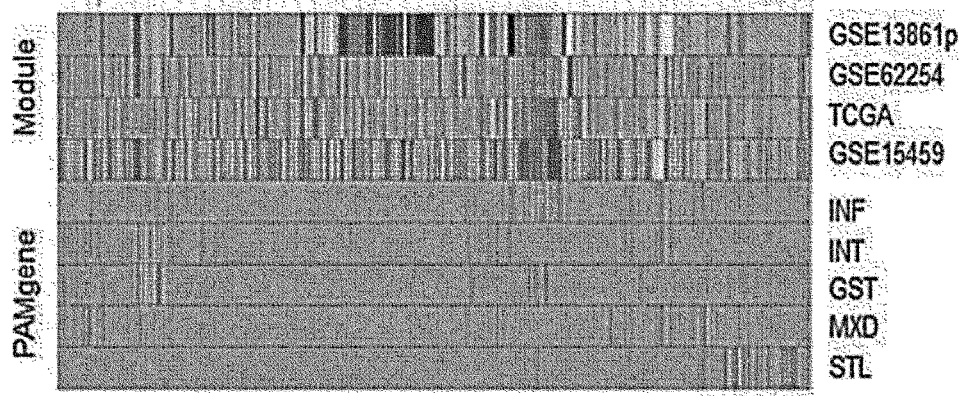
Fig. 4D
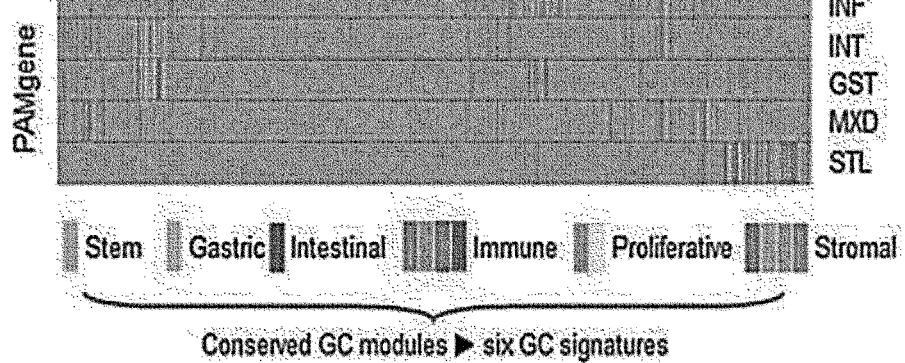
Fig. 4E
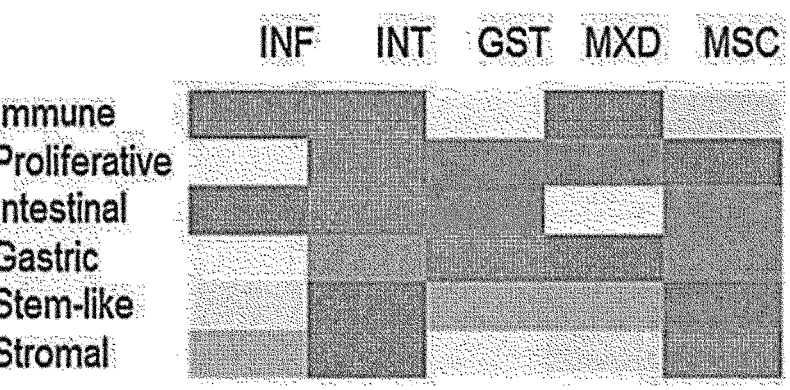

Fig. 7A  Fig. 7B  Fig. 7C  Fig. 7D
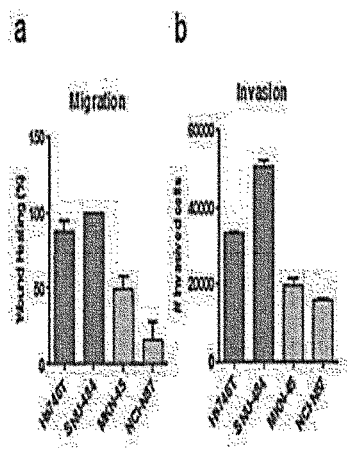 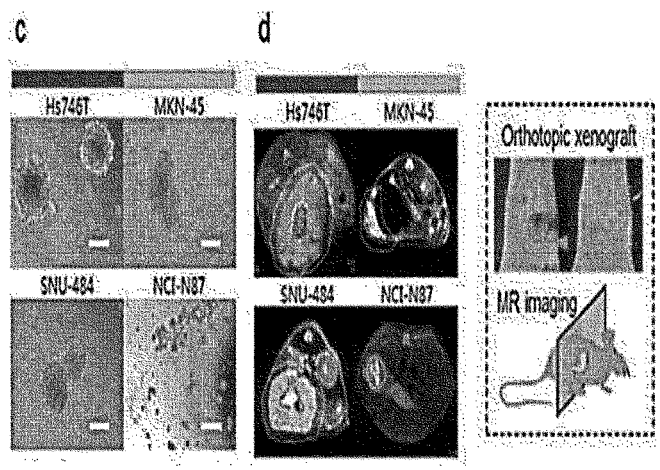
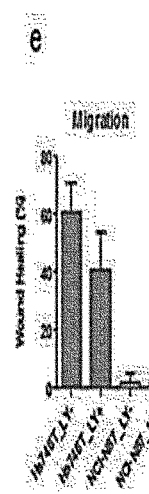 
Fig. 7E  Fig. 7F  Fig. 7G  Fig. 7H  Fig. 7I Fig. 8A
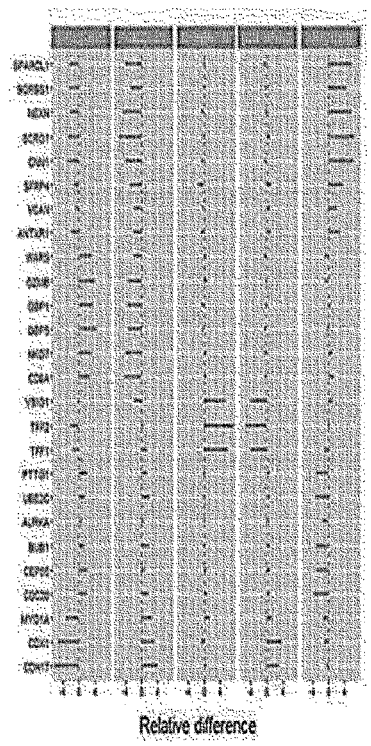
Fig. 8B
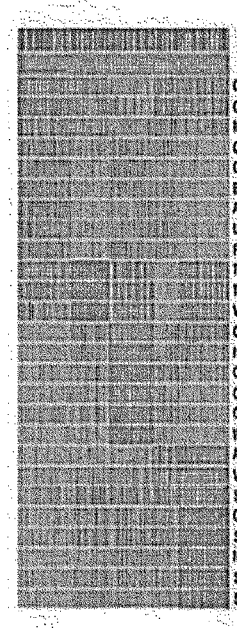
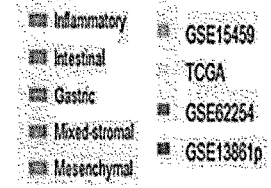
Fig. 8C
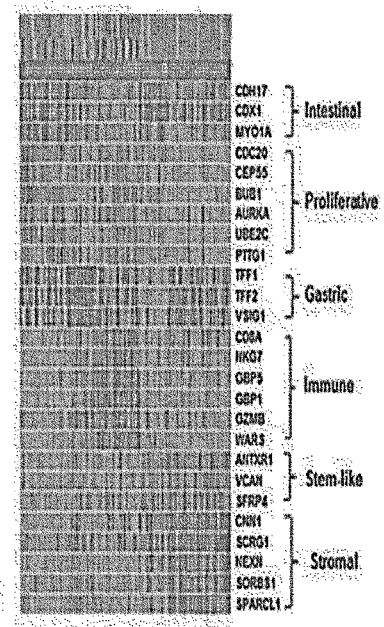
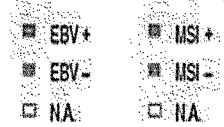
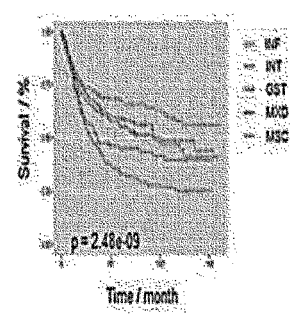
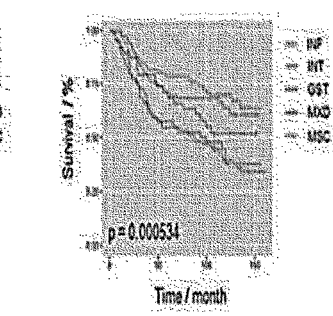
Fig. 8D    Fig. 8E

GROUP CLASSIFICATION AND PROGNOSIS PREDICTION SYSTEM BASED ON BIOLOGICAL CHARACTERISTICS OF GASTRIC CANCER

RELATED APPLICATIONS

This application is a National Phase of PCT Patent Application No. PCT/KR2018/004732 having International filing date of Apr. 24, 2018, which claims the benefit of priority of Korean Patent Application No. 10-2017-0052365 filed on Apr. 24, 2017. The contents of the above applications are all incorporated by reference as if fully set forth herein in their entirety.

FIELD AND BACKGROUND OF THE INVENTION

The present invention relates to a group classification and prognosis prediction system based on biological characteristics of gastric cancer.

Globally, gastric cancer is the third highest cause of cancer-related mortality and is the most common cancer particularly in Korea except for thyroid cancer, which is known to have a relatively good prognosis. In Korea, the survival rate of patients with gastric cancer has been increased due to early detection through national health examination, surgery standardization, and the discovery of anti-cancer therapeutic agents or the like, but despite the currently standardized treatment, about a half of patients with stage II and III advanced gastric cancer experience recurrence.

Cancer has been recognized as genomic disorder, and efforts have been made to classify cancer according to molecular and biological characteristics in line with the development of genetic testing technologies, such as next generation sequencing (NGS), instead of classifying cancer according to existing anatomical and pathological phenotypes. It has recently been reported in the Cancer Genome Atlas (TCGA) project that gastric cancer can be largely classified into four types according to various molecular characteristics thereof. This indicates that, even with the same clinical stage in an anatomical sense, prognoses and the degree of chemotherapy benefit may differ according to molecular and biological characteristics.

According to recently reported TCGA project results of 295 gastric cancer patients, gastric cancer is classified as four types: ① Epstein-Barr virus positive (EBV positive); ② microsatellite instability-high (MSI-H); ③ chromosomal instability (CIN); and ④ genomically stable (GS). Through this massive cancer genome sequencing, it can be seen that gastric cancer is divided into heterogeneous subgroups that are molecular-genetically distinguished, rather than having one cancer type. Thus, it suggests that to realize the personalized treatment of gastric cancer, it is necessary to identify subtypes based on molecular-genetic and pathological characteristics, discover corresponding target genes, and apply treatment accordingly. In addition, according to gastric cancer research results, it is reported that the prognosis of gastric cancer can be classified according to the subtype of gastric cancer.

If the prognosis of patients after chemotherapy treatment following gastric cancer surgery can be predicted, it will be a ground data capable of establishing a treatment strategy suitable for each prognosis. Currently, in standardized treatment practices, postoperative adjuvant chemotherapy treatment is used in all patients with stage II and III advanced gastric cancer. This, however, may be an undertreatment in groups with bad prognoses. Therefore, it may have a clinical significance for patient groups with poor prognoses if it were possible to develop strategies for other additional treatment methods in addition to the current standard treatment.

Since 2010, it has been discovered that in the case of stage II and III advanced gastric cancer, adjuvant chemotherapy treatment after standardized D2 gastrectomy increases the survival rate of gastric cancer patients, and currently, this corresponds to standard therapy. Traditionally, gastric cancer has been classified according to anatomic and pathologic phenotypes thereof, and cases of stage II or higher according to TNM stage classification receive chemotherapy treatments, but currently, there is no other method of predicting a prognosis according to chemotherapy treatment than TNM stage classification.

SUMMARY OF THE INVENTION

An object of the present invention is to provide a composition for predicting the prognosis of advanced gastric cancer, the composition based on a quantified value of an mRNA expression level of a target gene group, through which the postoperative prognosis of a patient with advanced gastric cancer (Stage II and III: based on AJCC $6^{th}$ Edition) is predictable.

Another object of the present invention is to provide a method of providing information for predicting a prognosis in terms of the survival rate of patients, the method based on a quantified value of an mRNA expression level of a target gene group, through which the postoperative prognosis of an advanced gastric cancer patient is predictable.

Still another object of the present invention is to provide a method of predicting a prognosis in terms of the survival rate of patients, the method based on a quantified value of an mRNA expression level of a target gene group, through which the postoperative prognosis of an advanced gastric cancer patient is predictable.

According to an aspect of the present invention, provided is a composition for predicting a prognosis of stage II and III advanced gastric cancer, the composition including: an agent for measuring an mRNA expression level of a target gene group including TFF1, TFF2, VSIG1, CNN1, NEXN, SCRG1, SORBS1, SPARCL1, AURKA, BUB1, CDC20, CEP55, PTTG1, UBE2C, CD8A, GBP1, GBP5, GZMB, NKG7, WARS, ANTXR1, SFRP4, VCAN, CDH17, CDX1, and MYO1A; and an agent for measuring an mRNA expression level of a reference gene group including ACTB, ATP5E, GPX1, UBB, and HPRT1.

The present invention also provides a kit for predicting a prognosis of stage II and III advanced gastric cancer, the kit including the above-described composition.

The present invention also provides a method of providing information for predicting a prognosis of stage II and III gastric cancer or a method of predicting a prognosis of stage II and III gastric cancer, each of the methods including:

in a sufficiently statistically significant number of reference samples and biological samples obtained from stage II and III advanced gastric cancer patients, measuring mRNA expression levels of a target gene group and a reference gene group, the target gene group including: a gastric signature consisting of TFF1, TFF2, and VSIG1; a mesenchymal signature consisting of CNN1, NEXN, SCRG1, SORBS1, and SPARCL1; a proliferative signature consisting of AURKA, BUB1, CDC20, CEP55, PTTG1, and UBE2C; an immune signature consisting of CD8A, GBP1, GBP5, GZMB, NKG7, and WARS; a stem-like signature consisting of ANTXR1, SFRP4, and VCAN; and an intestinal signature consisting of CDH17, CDX1, and MYO1A, and the reference gene group including ACTB, ATP5E, GPX1, UBB, and HPRT1;

calculating ΔCq values of the target gene groups of the reference samples and the biological samples according to Equation 1 below and inputting the values to a computer program; and performing non-negative matrix factorization (NMF) and NMF-based clustering on the values input to the computer program to be classified into a plurality of clusters, calculating a score value (SV) by applying a score ($d'_{ik}$) of the target gene group in each cluster to Equation 2 below, classifying the clusters into an intestinal molecular subtype, an inflammatory molecular subtype, a mesenchymal molecular subtype, a mixed-stromal molecular subtype, and a gastric molecular subtype, and predicting a prognosis of the molecular subtype to which the biological sample belongs by analyzing the prognosis in terms of overall survival, wherein the molecular subtypes of gastric cancer are classified such that a cluster in which the SV of the gastric signature is a maximum value is determined as a gastric molecular subtype; among clusters except for the cluster determined as the gastric molecular subtype, a cluster in which the SV of the mesenchymal signature is a maximum value and the SV of the proliferative signature is a minimum value is determined as a mesenchymal molecular subtype; among clusters except for the cluster determined as the gastric molecular subtype and the cluster determined as the mesenchymal molecular subtype, a cluster in which the SV of the immune signature is a maximum value and the SV of the intestinal signature is a minimum value is determined as an inflammatory molecular subtype; among clusters except for the cluster determined as the gastric molecular subtype, the cluster determined as the mesenchymal molecular subtype, and the cluster determined as the inflammatory molecular subtype, a cluster in which the SV of the stem-like signature is a maximum value is determined as a mixed-stromal molecular subtype; and a last remaining cluster is determined as an intestinal molecular subtype, and a prognosis of gastric cancer is predicted, in terms of overall survival, such that one classified as the inflammatory molecular subtype is predicted as a good prognosis group; those classified as the intestinal molecular subtype and the gastric molecular subtype are predicted as intermediate prognosis group; and those classified as the mixed-stromal molecular subtype and the mesenchymal molecular subtype are predicted as bad prognosis group:

$$\Delta Cq = (Cq \text{ value of target gene}) - (Cq \text{ mean of reference gene group}) \qquad [\text{Equation 1}]$$

wherein the Cq mean of the reference gene group denotes a mean of Cq values of the reference gene group including ACTB, ATP5E, GPX1, UBB, and HPRT1, $$SV \text{ (Score Value)} = \frac{1}{t} \sum_{i \in SN_\theta} d'_{ik} \qquad [\text{Equation 2}]$$

wherein SV is an expression mean of each signature in the clusters obtained from NMF-based clustering, t is the number of genes (i) belonging to each signature, $SN_\theta$ is signature (θ=6), k denotes the number of clusters, which is an integer of 2 to 7, and $d'_{ik}$ denotes a score based on a distance between the median of total gene and a mean of each cluster and is obtained according to Equation 3 below:

$$d'_{ik} = \text{sign}(d_{ik})(|d_{ik}| - \Delta)_+ \qquad [\text{Equation 3}]$$

wherein a critical value (Δ) is set at 0.1 so that genes with no specificity according to molecular subtype are converged to 0, sign($d_{ik}$) denotes a sign of $d_{ik}$, and $d_{ik}$ is obtained according to Equation 4 below:

$$d_{ik} = \frac{\overline{x}_{ik} - \overline{x}_i}{m_k(s_i + s_0)}, \qquad [\text{Equation 4}]$$

$$s_i^2 = \frac{1}{n-k} \sum_{k=1}^{5} \sum_{j \in C_k} (x_{ij} - \overline{x}_{ik})^2$$

wherein $$\overline{x}_{ik} = \sum_{j \in C_k} \frac{x_{ij}}{n_k}$$

is an expression mean of the (ith) gene in molecular subtype (k), $$\overline{x}_i = \sum_{j=1}^{n} \frac{x_{ij}}{n}$$

is a total mean of the same (ith) gene, $m_k$ denotes a degree of freedom $$\left( m_k = \sqrt{\frac{1}{n_k} + \frac{1}{n}} \right)$$

for correcting a standard error of $\overline{x}_{ik} - \overline{x}_i$, $s_i$ denotes a standard deviation of the entire sample of the (i) gene belonging to molecular subtype (k), and $s_0$ denotes a median of $s_i$.

According to the present invention, an algorithm capable of predicting the prognosis of advanced gastric cancer in terms of overall survival by using a quantified value of an mRNA expression level of a target gene group, through which the prognosis is predictable, has been developed and this can be used as auxiliary information for determining a treatment method of a gastric cancer patient.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the attached drawings, in which:

FIGS. 2A-2D illustrate NMF consensus clustering results obtained using Classifier-PAM932, wherein FIG. 2A illustrates a heatmap (GSE13861p) of the Training set I characterized by the Molecular Signatures Database (MSigDB) and gene sets (digestion, spasmolytic polypeptide-expressing metaplasia (SPEM), intestinal metaplasia (IM), immune system, stroma, epithelial-mesenchymal transition (EMT), and cell cycle) analyzed in previous studies, which is the result of verifying NMF consensus clustering using independent test set I and Classifier-PAM932 (GST, gastric subtype; INF, inflammatory; MSC, mesenchymal; INT, intestinal; MXD, mixed-stromal molecular subtypes), and FIGS. 2B, 2C, and 2D illustrate heatmaps of GSE62254 (Asian Cancer Research Group, ACRG), TCGA, and GSE15459 (Singapore), respectively, and the previously obtained subtype information is co-provided above each heat map.

FIGS. 3A-3C illustrate NMF clustering, wherein samples were designated using (FIG. 3A) consensus maps with cluster numbers (k) 2 to 7 and the following dispersion cut-offs, (FIG. 3B) Cophenetic correlation coefficients, and (FIG. 3C) silhouette widths, at SD=0.8, SD=0.9, and SD=1.0.

FIGS. 4A-4B illustrate subtype-defining gastric cancer signatures discovered by WGCNA analysis, wherein FIG. 4A (upper view) illustrates a dendrogram of GSE13861p, FIG. 4A (middle view) illustrates a module detected in GSE13861p and the corresponding module maps of GSE62254, TCGA, and GSE15459, in which when a module of each of a plurality of cohorts, which are an independent test set, shared common genes with the module of GSE13861p, the color of the module was one-to-one adjusted for visual convenience, FIG. 4A (lower view) illustrates mapping results of the top 25% high-scoring PAMgenes of each subtype in a training set, and FIG. 4A (lowest view) illustrates six GC signatures represented by a combination of conserved modules in GC, and FIG. 4B illustrates the correlation between GC subtypes and six GC signatures as analyzed using Spearman's correlation, in which red represents modules positively correlated with corresponding subtype, and blue represents modules negatively correlated with corresponding subtype.

FIGS. 6A-6B illustrate gastric cancer stromal signatures (n=26) investigated using cancer cell lines, wherein FIG. 6A is a heatmap showing GC subtypes in a training set combined with cancer cell line data, and FIG. 6B is a heatmap arranged with a stromal module eigengene in which Hs746, SNU-484 (MSC), MKN-45, and NCI-N87 (INT) cell lines are represented by arrowheads.

FIGS. 7A-7I compare MSC and INT types of GC lines by (FIG. 7A) in vitro scratch wound-healing assay, (FIG. 7B) invasion assay, (FIG. 7C) in vitro tumor spheroid formation assay (scale bars, 100 µm), and (FIG. 7D) in vivo orthotopic tumorigenesis (n=3), in which the diffused growth of Hs746T and SNU-48 tumors and the confinement of MKN-45 and NCI-N87 tumors are bordered by white dotted lines in MRI images (axial section), images in the black-dotted box depict the orthotopic model construction, and suppression of the stromal behavior of Hs746T cells by treatment with a TGF-β inhibitor (LY2157299 (LY)) was observed through in vitro scratch wound-healing assay (FIG. 7E), invasion assay (FIG. 7F), and in vitro tumor spheroid formation assay (FIG. 7G), and illustrates in vivo drug-resistance assay results measuring the tumor growth of Hs746t tumors (FIG. 7H) and NCI-N87 tumors (FIG. 7I) in a xenograft mouse model (n=8) under the co-administration of a TGF-β inhibitor during combination drug therapy (oxaliplatin and fluorouracil) ($P<0.05$).

FIGS. 8A-8E illustrate five molecular subtypes classified by miniClassifier26 in GC, wherein FIG. 8A illustrates relative differences of 26 representative genes for the five molecular subtypes in PAM, FIG. 8B is a heatmap (merged using the ComBat method, N=1259; GSE13861p, GSE15459, TCGA, and GSE62254) of NMF-based clustering (26 genes) for GC microarray data, FIG. 8C is a heatmap of NMF-based clustering (26 genes) for GC qPCR data, FIGS. 8D and 8E illustrate overall survival (OS) rates of the 5 molecular subtypes clustered in (FIG. 8B) and (FIG. 8C), FIG. 8D illustrates an OS curve of 1198 samples, except for 61 samples with no clinical information, among Merged1259 cohort samples, in which the five-year survival rate of each molecular subtype is 67.3% for INF (95% confidence interval: 61.3-73.9%), 58.8% for INT (95% confidence interval: 52.9-65.4%), 55.3% for GST (95% confidence interval: 48.2-63.4%), 45.0% for MXD (95% confidence interval: 36.5-55.4%), and 33.0% for MSC (95% confidence interval: 27.3-40.0%), and FIG. 8E is a five-year OS curve of a group classified as 26 genes from qPCR measurement results of qPCR325 cohorts, in which the five-year survival rate of each molecular subtype is 78.5% for INF (95% confidence interval: 69.4-88.8%), 70.7% for INT (95% confidence interval: 61.1-81.8%), 68.4% for GST (95% confidence interval: 55.1-84.9%), 54.6% for MXD (95% confidence interval: 41.7-71.4%), and 57.5% for MSC (95% confidence interval: 48.4-68.2%).

DESCRIPTION OF SPECIFIC EMBODIMENTS OF THE INVENTION

Figure 1:
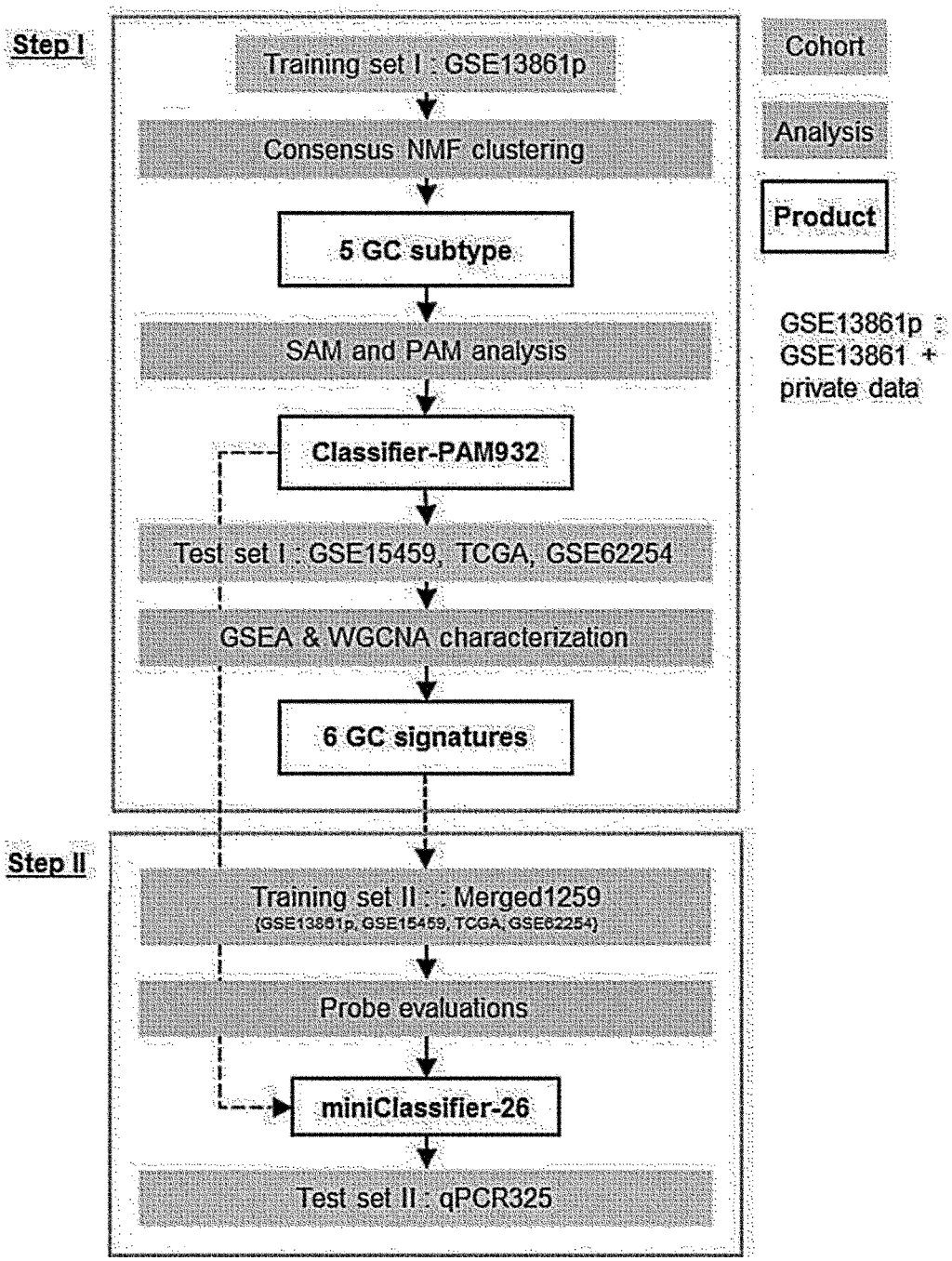
FIG. 1 is a flowchart of the experimental analysis of the present invention, wherein process I is a process of identifying gastric cancer (GC) molecular subtypes, a classifier, and GC signatures, as a series of analysis results (NMF, non-negative matrix factorization; SAM, significance analysis of microarrays; PAM, prediction analysis of microarrays; GSEA, gene-set enrichment analysis; WGCNA, weighted gene co-expression network analysis), and process II is a process of identifying GC signatures and molecular subtypes for maximizing clinical efficiency through the construction of a series of probes for profiling the expression of GC signatures, miniClassifier-26, in patient samples.

Hereinafter, the configuration of the present invention will be described in detail.

The present invention relates to a composition for predicting the prognosis of stage II and III advanced gastric cancer, the composition including:

an agent for measuring an mRNA expression level of a target gene group including TFF1, TFF2, VSIG1, CNN1, NEXN, SCRG1, SORBS1, SPARCL1, AURKA, BUB1, CDC20, CEP55, PTTG1, UBE2C, CD8A, GBP1, GBP5, GZMB, NKG7, WARS, ANTXR1, SFRP4, VCAN, CDH17, CDX1, and MYO1A; and an agent for measuring an mRNA expression level of a reference gene group including ACTB, ATP5E, GPX1, UBB, and HPRT1.

The composition for predicting the prognosis of stage II and III gastric cancer of the present invention may be used for predicting the prognosis of a patient with advanced gastric cancer in terms of a survival rate by measuring the mRNA expression level of the target gene group.

As used herein, the term "advanced gastric cancer" refers to gastric cancer corresponding to stage II to stage III based on the AJCC $6^{th}$ edition.

As used herein, the term "target gene" or "marker gene" is used interchangeably in the specification and refers to a marker capable of distinguishing between normal and pathological conditions, predicting the five-year survival rate after treatment, or making objective predictions on therapeutic responses. In the present invention, the target gene or the marker gene is a gene suitable for use in predicting the prognosis of advanced gastric cancer and a gene exhibiting a varying mRNA expression level which increases or decreases depending on the prognosis. According to one embodiment of the present invention, by securing a statistical significance for gastric cancer with heterogeneity from the microarray data and qPCR data of fresh-frozen tissue and the qPCR data of paraffin-embedded sample specimens, 26 types of genes, i.e., TFF1, TFF2, VSIG1, CNN1, NEXN, SCRG1, SORBS1, SPARCL1, AURKA, BUB1, CDC20, CEP55, PTTG1, UBE2C, CD8A, GBP1, GBP5, GZMB, NKG7, WARS, ANTXR1, SFRP4, VCAN, CDH17, CDX1, and MYO1A, which can be classified into five molecular subtypes, i.e., an intestinal molecular subtype, an inflammatory molecular subtype, a mesenchymal molecular subtype, a mixed-stromal molecular subtype, and a gastric molecular subtype, were selected.

As used herein, the term "reference gene" refers to a gene which is expressed stably at all times. That is, the reference gene as a gene constantly expressed in any tissue is used to examine an expression amount of a marker gene by comparing an expression amount of the reference gene with the expression amount of the marker gene. That is, since there is a qualitative difference and variations according to storage institute for each sample, it is difficult to identify a biological variation based on a measured gene expression amount. Thus, a gene expression level ($\Delta$Cq) between samples is determined through normalization. As a general normalization method, a method using Quantile, a global normalization method, a method using a reference gene, or the like may be used, but the present invention uses normalization using a reference gene. In addition, since the use of a single gene as a reference gene has low accuracy, a reference gene suitable for tissue characteristics may be selected by selecting a plurality of genes and examining a variation. In the present invention, genes that are disclosed in references related to gastric cancer or used in existing, currently available products are selected, and the suitability of the selected genes is evaluated, and a suitable selected gene is used as a reference gene. According to one embodiment of the present invention, with respect to 21 reference genes disclosed in references, the tissue of cancer such as esophageal cancer, pancreatic cancer, gastric cancer, colon cancer, or the like was compared with normal tissue, and a gene having the smallest variation according to qPCR was selected as a reference gene. Next, ACTB, ATP5E, GPX1, UBB, and HPRT1 were selected as reference genes used in commercially available products and subjected to qPCR, and finally, a gene group consisting of ACTB, ATP5E, GPX1, UBB, and HPRT1 was used as a reference gene used to predict the prognosis of advanced gastric cancer or the possibility of responding to an anticancer agent.

As used herein, the expression "measuring an mRNA expression level" refers to a process of identifying mRNA expression levels of prognostic marker genes in a biological sample to predict the prognosis of advanced gastric cancer and means measurement of the amount of mRNA. For example, the measuring process may be performed by quantitative real-time polymerase chain reaction (qPCR), but the present invention is not limited thereto.

In the composition according to the present invention, an agent for measuring an mRNA expression level of a prognostic marker gene includes a primer, probe, or antisense nucleotide that specifically binds to mRNA of the prognostic marker gene. Information of prognostic marker genes according to the present invention are known in GenBank, UniProt, and the like, and thus a primer, probe, or antisense nucleotide that specifically binds to mRNA of a gene may be easily designed by one of ordinary skill in the art based on this information.

As used herein, the term "primer" refers to a fragment that recognizes a target gene sequence, and includes a pair of forward and reverse primers, but is preferably a pair of primers that provide analysis results with specificity and sensitivity. In the case of a primer, the nucleic acid sequence of which is inconsistent with a non-target sequence present in a sample and thus amplifies only a target gene sequence containing a complementary primer binding site and does not cause non-specific amplification, high specificity may be imparted. According to one embodiment of the present invention, primer sets listed in SEQ ID NOS: 1 to 62 may be used. Primer sets of each of the target gene group and the reference gene group are listed in Tables 1 and 2 below.

As used herein, the term "probe" refers to a substance capable of specifically binding to a target material to be detected in a sample and specifically identifying the presence of a target material in a sample through the binding. The type of probe may be any material commonly used in the art without limitation, but preferably, it may be peptide nucleic acid (PNA), locked nucleic acid (LNA), a peptide, a polypeptide, a protein, RNA, or DNA. More particularly, the probe, which is a biomaterial, includes a material derived from a living organism, an analogue thereof, or a material produced in vitro, and examples of the probe include an enzyme, a protein, an antibody, a microorganism, an animal or plant cell and organ, a neuron, DNA, and RNA, examples of DNA include cDNA, genomic DNA, and an oligonucleotide, and examples of RNA include genomic RNA, mRNA, and an oligonucleotide, and examples of the protein include an antibody, an antigen, an enzyme, a peptide, and the like. According to one embodiment of the present invention, probes set forth in SEQ ID NOS: 63 to 93 may be used. Preferably, the probe may be fluorescently labeled. Probes of each of the target gene group and the reference gene group are listed in Tables 1 and 2 below.

As used herein, the term "antisense" refers to an oligomer with a sequence of nucleotide bases and a backbone between sub-units that allow the antisense oligomer to hybridize with a target sequence in RNA by Watson-Crick base pairing, to form a RNA:oligomer heterodimer within the target sequence, typically with mRNA. The oligomer may have exact sequence complementarity or near-complementarity to the target sequence.

As used herein, the term "predicting the prognosis" is intended to include determining the susceptibility of a subject to a particular disease or disorder, determining the prognosis (e.g., identifying a pre-metastatic or metastatic cancerous condition, determining the stage of cancer, or determining the response of cancer to treatment) of a subject with a particular disease or disorder, or therametrics (e.g., monitoring the condition of an object of treatment to provide information about therapeutic efficacy). The present invention aims to predict the postoperative prognosis of gastric cancer patients in terms of overall survival.

According to one embodiment of the present invention, the target gene is selected as follows. First, highly interconnected five subtypes with distinct molecular characteristics are determined by performing consensus-based NMF on advanced gastric cancer tissue, and subtype-specific gene groups are selected.

The NMF (nonnegative matrix factorization), which is a dimension reduction method, is a method of grouping samples with a similar high expression pattern together as one subtype.

Figure 11:
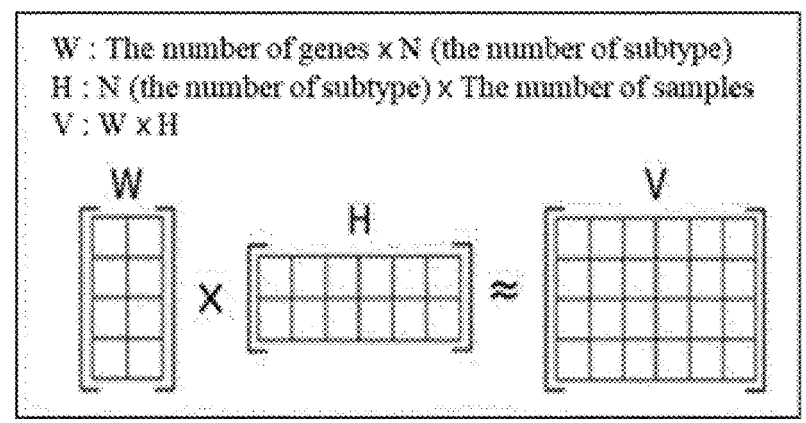
FIG. 11 illustrates a method for determining the molecular subtypes of gastric cancer using a dimension reduction method.

To determine the molecular subtypes of gastric cancer, one matrix is factorized into two non-negative matrices using a dimension reduction method, thereby isolating common bases through an NMF algorithm. When an actual information group is V and matrices to be separated are W and H, the condition, V=WH, is satisfied, and in this case, W denotes a base matrix and H denotes an encoding matrix. V is a sum of the bases of W, and V is a matrix with a size of (n×m), W is a matrix with a size of (n×r), and H is a matrix with a size of (r×m). Since high-order data matrices are decomposed into low-order coefficient matrices and a base matrix, and each matrix has sparse characteristics, part-based representation is possible. Through this algorithm, gastric cancer may be grouped according to similarity for use in the classification of gastric cancer subtypes (see FIG. 11).

Clusters suitable for gastric cancer subtypes are selected based on a consensus map and a cophenetic graph, by using the NMF package of the R program. Consensus clustering of k (the number of clusters) in each of the standard deviations (SD=0.8, 0.9, and 1.0) is confirmed to finally select the number of gastric cancer subtypes (see FIG. 3). According to one embodiment of the present invention, k was set at 5.

As a result of acquiring the characteristics of each subtype from a biological gene set to identify molecular heterogeneity, gastric cancer is classified into five subtypes, i.e., an intestinal molecular subtype, an inflammatory molecular subtype, a mesenchymal molecular subtype, a mixed-stromal molecular subtype, and a gastric molecular subtype.

As a result of conducting survival analysis for the five molecular subtypes using a Cox proportional hazard model, the inflammatory molecular subtype exhibits a good prognosis, the intestinal and gastric molecular subtypes exhibit an intermediate prognosis, and the mixed-stromal and mesenchymal molecular subtypes exhibit a poor prognosis, all in terms of overall survival.

Meanwhile, to analyze the biological characteristics of gastric cancer, weighted correlation network analysis (WGCNA) is used. The WGCNA is an analytical technique for clustering genes based on an interconnection in expression between genes exhibiting similar expression patterns, in which modules (clusters of highly interconnected genes) are searched for through WGCNA, and signatures, on which gastric cancer characteristics are reflected, are selected according to the nature of the modules and a correlation between the modules. According to one embodiment of the present invention, six signatures stably conserved in gastric cancer, i.e., a gastric signature consisting of TFF1, TFF2, and VSIG1; a mesenchymal signature consisting of CNN1, NEXN, SCRG1, SORBS1, and SPARCL1; a proliferative signature consisting of AURKA, BUB1, CDC20, CEP55, PTTG1, and UBE2C; an immune signature consisting of CD8A, GBP1, GBP5, GZMB, NKG7, and WARS; a stem-like signature consisting of ANTXR1, SFRP4, and VCAN; and an intestinal signature consisting of CDH17, CDX1, and MYO1A, were identified.

The correlation between representative genes of the six signatures and the five gastric cancer molecular subtypes was confirmed by comparative analysis by Spearman correlation. Through this, commonly conserved genes were selected, and then 26 genes, i.e., TFF1, TFF2, VSIG1, CNN1, NEXN, SCRG1, SORBS1, SPARCL1, AURKA, BUB1, CDC20, CEP55, PTTG1, UBE2C, CD8A, GBP1, GBP5, GZMB, NKG7, WARS, ANTXR1, SFRP4, VCAN, CDH17, CDX1, and MYO1A, exhibiting stable expression results for each sampling method (fresh-frozen, FFPE) and each expression measurement platform (microarray, qPCR), were selected.

The selected 26 genes are denoted as a target gene group, and an expression mean of each signature corresponding to each target gene group is calculated using a score ($d'_{ik}$) of each target gene, and the result is used to identify molecular subtypes.

When the molecular subtypes of gastric cancer are determined as above, a prognosis is predicted based on a survival curve of each molecular subtype. For example, the molecular subtypes are classified into a good prognosis group, an intermediate prognosis group, and a bad prognosis group, all in terms of overall survival. In particular, in terms of overall survival, the inflammatory molecular subtype is predicted as a good prognosis group, the intestinal and gastric molecular subtypes are predicted as intermediate prognosis group, and the mixed-stromal and mesenchymal molecular subtypes are predicted as bad prognosis group.

The composition for predicting the prognosis of stage II and III gastric cancer of the present invention may further include a pharmaceutically acceptable carrier.

The pharmaceutically acceptable carrier includes carriers and vehicles commonly used in the medical field, and examples thereof include, but are not limited to, ion exchange resins, alumina, aluminum stearate, lecithin, serum proteins (e.g., human serum albumin), buffer substances (e.g., various phosphates, glycine, sorbic acid, potassium sorbate, and partial glyceride mixtures of saturated vegetable fatty acids), water, salts or electrolytes (e.g., protamine sulfate, disodium hydrogen phosphate, potassium hydrogen phosphate, sodium chloride, and zinc salts), colloidal silica, magnesium trisilicate, polyvinyl pyrrolidone, cellulose-based substrates, polyethylene glycol, sodium carboxymethylcellulose, polyarylate, waxes, polyethylene glycol, and wool fat.

In addition, the composition of the present invention may further include, in addition to the above-described components, a lubricant, a wetting agent, an emulsifying agent, a suspension agent, a preservative, or the like.

The present invention also provides a kit for predicting the prognosis of stage II and III gastric cancer, which includes a composition for predicting the prognosis of stage II and III gastric cancer.

For example, the kit may be a quantitative real-time polymerase chain reaction (qPCR) kit or the like.

The kit for predicting the prognosis of stage II and III gastric cancer may further include one or more types of other differently formulated compositions, solutions or devices suitable for an assay method. Preferably, the kit further includes an essential element needed for qPCR. The qPCR kit includes a primer pair specific to a gene encoding a marker protein. Primers are nucleotides having a sequence specific to a nucleic acid sequence of the gene and may have a length of about 7 bp to about 50 bp, more preferably, about 10 bp to about 30 bp. In addition, the qPCR kit may include primers specific to a nucleic acid sequence of a control gene. In addition, the qPCR kit may include a test tube or other appropriate container, a reaction buffer (of various pH and magnesium concentrations), deoxynucleotides (dNTPs), enzymes such as Taq-polymerase and reverse transcriptase, a DNase inhibitor, an RNase inhibitor, DEPC-water, sterilized water, and the like.

In addition, the kit for predicting the prognosis of stage II and III gastric cancer of the present invention may include an essential element needed for performing DNA chip. A DNA chip kit may include a substrate to which a gene or cDNA or an oligonucleotide that corresponds to a fragment of the gene is attached, and a reagent, agent, enzyme, or the like for producing a fluorescent labeling probe. In addition, the substrate may include a control gene or cDNA or an oligonucleotide that corresponds to a fragment of the gene.

The present invention also provides a method of providing information for predicting the prognosis of stage II and III gastric cancer or a method of predicting the prognosis of stage II and III gastric cancer, each of the methods including:

in a sufficiently statistically significant number of reference samples and biological samples obtained from stage II and III advanced gastric cancer patients, measuring mRNA expression levels of a target gene group including: a gastric signature consisting of TFF1, TFF2, and VSIG1; a mesenchymal signature consisting of CNN1, NEXN, SCRG1, SORBS1, and SPARCL1; a proliferative signature consisting of AURKA, BUB1, CDC20, CEP55, PTTG1, and UBE2C; an immune signature consisting of CD8A, GBP1, GBP5, GZMB, NKG7, and WARS; a stem-like signature consisting of ANTXR1, SFRP4, and VCAN; and an intestinal signature consisting of CDH17, CDX1, and MYO1A, and a reference gene group including ACTB, ATP5E, GPX1, UBB, and HPRT1;

calculating ΔCq values of the target gene groups of the reference samples and the biological samples according to Equation 1 below and inputting the values to a computer program; and performing non-negative matrix factorization (NMF) and NMF-based clustering on the values input to the computer program to be classified into a plurality of clusters, calculating a score value (SV) by applying the score ($d'_{ik}$) of the target gene group in each cluster to Equation 2 below, classifying the clusters into an intestinal molecular subtype, an inflammatory molecular subtype, a mesenchymal molecular subtype, a mixed-stromal molecular subtype, and a gastric molecular subtype, and predicting a prognosis of the molecular subtype to which the biological sample belongs by analyzing the prognosis in terms of overall survival, wherein the molecular subtypes of gastric cancer are classified such that a cluster in which the SV of the gastric signature is a maximum value is determined as a gastric molecular subtype; among clusters except for the cluster determined as the gastric molecular subtype, a cluster in which the SV of the mesenchymal signature is a maximum value and the SV of the proliferative signature is a minimum value is determined as a mesenchymal molecular subtype; among clusters except for the cluster determined as the gastric molecular subtype and the cluster determined as the mesenchymal molecular subtype, a cluster in which the SV of the immune signature is a maximum value and the SV of the intestinal signature is a minimum value is determined as an inflammatory molecular subtype; among clusters except for the cluster determined as the gastric molecular subtype, the cluster determined as the mesenchymal molecular subtype, and the cluster determined as the inflammatory molecular subtype, a cluster in which the SV of the stem-like signature is a maximum value is determined as a mixed-stromal molecular subtype; and the last remaining cluster is determined as an intestinal molecular subtype, and a prognosis of gastric cancer is predicted, in terms of overall survival, such that one classified as the inflammatory molecular subtype is predicted as a good prognosis group; those classified as the intestinal molecular subtype and the gastric molecular subtype are predicted as intermediate prognosis group; and those classified as the mixed-stromal molecular subtype and the mesenchymal molecular subtype are predicted as bad prognosis group:

$$\Delta Cq = (Cq \text{ value of target gene}) - (Cq \text{ mean of reference gene group}) \quad \text{[Equation 1]}$$

wherein the Cq mean of the reference gene group denotes a mean of Cq values of the reference gene group including ACTB, ATP5E, GPX1, UBB, and HPRT1, $$SV \text{ (Score Value)} = \frac{1}{t} \sum_{i \in SN_\theta} d'_{ik} \quad \text{[Equation 2]}$$

wherein SV is an expression mean of each signature in the clusters obtained from NMF-based clustering, t is the number of genes (i) belonging to each signature, $SN_\theta$ is signature (θ=6), k denotes the number of clusters, which is an integer of 2 to 7, and $d'_{ik}$ denotes a score based on a distance between a total mean of each gene and a mean of each cluster and is obtained according to Equation 3 below:

$$d'_{ik} = \text{sign}(d_{ik})(|d_{ik}| - \Delta)_+ \quad \text{[Equation 3]}$$

wherein a critical value (Δ) is set at 0.1 so that genes with no specificity according to molecular subtype are converged to 0, sign($d_{ik}$) denotes a sign of $d_{ik}$, and $d_{ik}$ is obtained according to Equation 4 below:

$$d_{ik} = \frac{\bar{x}_{ik} - \bar{x}_i}{m_k(s_i + s_0)}, \quad \text{[Equation 4]}$$

$$s_i^2 = \frac{1}{n-k} \sum_{k=1}^{5} \sum_{j \in C_k} (x_{ij} - \bar{x}_{ik})^2$$

wherein $$\bar{x}_{ik} = \sum_{j \in C_k} \frac{x_{ij}}{n_k}$$

is an expression mean of the (ith) gene in molecular subtype (k), $$\bar{x}_i = \sum_{j=1}^{n} \frac{x_{ij}}{n}$$

is a total mean of the same (ith) gene, $m_k$ denotes a degree of freedom $$\left(m_k = \sqrt{\frac{1}{n_k} + \frac{1}{n}}\right)$$

for correcting a standard error of $\bar{x}_{ik}-\bar{x}_i$, $s_i$ denotes a standard deviation of the entire sample of the (i) gene belonging to molecular subtype (k), and $s_0$ denotes a median of $s_i$.

The method of providing information for predicting the prognosis of stage II and III gastric cancer, according to the present invention, will be described step by step in detail as follows.

The first process is a process of measuring an mRNA expression level of a target gene group in a certain number of reference samples obtained from stage II and III gastric tumors, measuring an mRNA expression level of a target gene group of a biological sample obtained from stage II and III gastric tumors, and inputting values corresponding to the mRNA expression levels of the target gene groups of the reference samples and the biological sample to a computer program.

The certain number, i.e., the number of reference samples sufficient to exhibit a statistical significance, refers to the number of samples satisfying p<0.01 when non-negative matrix factorization (NMF) is performed on the mRNA expression level of the target gene group.

In addition, the number of reference samples must be a number sufficient to exhibit a gene expression pattern differentiated according to NMF-based clustering and to be classified into a plurality of clusters.

The number of reference samples which satisfies these conditions may range from, preferably, 300 to 10,000.

Preferably, the mRNA expression level of the target gene group is measured by qPCR, and the mRNA expression level measured by qPCR is determined as ΔCq. The Cq value refers to the number of cycles at which amplification starts to remarkably increase during PCR processes performed at 95° C. for 10 minutes (initial denaturation); 40 times to 45 times at 95° C. for 10 seconds (denaturation); at 60° C. for 5 seconds (annealing); and then at 72° C. for 25 seconds (elongation).

The ΔCq value is calculated using a Cq mean of each of the target gene group and the reference gene group according to Equation 1 below:

ΔCq=(Cq value of target gene)−(Cq mean of reference gene group) [Equation 1]

wherein the Cq mean of the reference gene group denotes a mean of Cq values of the reference gene group including ACTB, ATP5E, GPX1, UBB, and HPRT1.

Thus, the ΔCq value is the value corresponding to the mRNA expression level of the target gene group, which is input to a computer program.

The second process is a process of performing NMF and NMF-based clustering on the ΔCq values of the target gene groups of the reference samples and the biological samples, which are input to a computer program, for classification into a plurality of clusters, calculating a score value (SV) by applying the score ($d'_{ik}$) of the target gene group in each cluster to Equation 2 below, classifying the clusters into an intestinal molecular subtype, an inflammatory molecular subtype, a mesenchymal molecular subtype, a mixed-stromal molecular subtype, and a gastric molecular subtype according to SV, and predicting a prognosis of the molecular subtype to which the biological sample belongs by analyzing the prognosis in terms of overall survival.

$$SV \text{ (Score Value)} = \frac{1}{t}\sum_{i \in SN_\theta} d'_{ik} \quad \text{[Equation 2]}$$

wherein SV is an expression mean of each signature in the clusters obtained from NMF-based clustering, t is the number of genes (i) belonging to each signature, $SN_\theta$ is signature (θ=6), k denotes the number of clusters, which is an integer of 2 to 7, and $d'_{ik}$ denotes a score based on a distance between a total mean of each gene and a mean of each cluster.

According to the present invention, k is preferably 5. That is, when k=5, it means five clusters obtained through NMF-based clustering.

According to the present invention, k is preferably 5. That is, when k=5, it means five clusters obtained through NMF-based clustering.

The score ($d'_{ik}$) is a score based on a distance between a total mean of each gene and a mean of each cluster, i.e., a t-statistic value of the same gene type (i), is normalized by applying a weight with respect to the expression amounts of sample genes belonging to the same molecular subtype, and is obtained by Equation 3 below using a statistical method commonly used in linear discriminant analysis (LDA):

$d'_{ik}=\text{sign}(d_{ik})(|d_{ik}|-\Delta)_+$ [Equation 3]

wherein a critical value (Δ) is set at 0.1 so that genes with no specificity according to molecular subtype are converged to 0, sign($d_{ik}$) denotes a sign of $d_{ik}$, and $d_{ik}$ is obtained according to Equation 4 below:

$$d_{ik} = \frac{\bar{x}_{ik} - \bar{x}_i}{m_k(s_i + s_0)}, \quad \text{[Equation 4]}$$

$$s_i^2 = \frac{1}{n-k}\sum_{k=1}^{5}\sum_{j \in C_k}(x_{ij} - \bar{x}_{ik})^2$$

wherein $$\bar{x}_{ik} = \sum_{j \in C_k} \frac{x_{ij}}{n_k}$$

is an expression mean of the (ith) gene in molecular subtype (k), $$\bar{x}_i = \sum_{j=1}^{n} \frac{x_{ij}}{n}$$

is a total mean of the same (ith) gene, $m_k$ denotes a degree of freedom $$\left(m_k = \sqrt{\frac{1}{n_k} + \frac{1}{n}}\right)$$

for correcting a standard error of $\overline{x}_{ik}$–$\overline{x}_i$, $s_i$ denotes a standard deviation of the entire sample of the (i) gene belonging to molecular subtype (k), and $s_0$ denotes a median of $s_i$.

In the score (d'$_{ik}$), positive numbers denote high gene expression, negative numbers denote low gene expression, and 0 denotes no change in gene expression. Thus, the more positive the score, the higher the gene expression, and the more negative the score, the lower the gene expression.

The molecular subtypes of gastric cancer are classified such that a cluster in which the SV of the gastric signature is a maximum value is determined as a gastric molecular subtype; among clusters except for the cluster determined as the gastric molecular subtype, a cluster in which the SV of the mesenchymal signature is a maximum value and the SV of the proliferative signature is a minimum value is determined as a mesenchymal molecular subtype; among clusters except for the cluster determined as the gastric molecular subtype and the cluster determined as the mesenchymal molecular subtype, a cluster in which the SV of the immune signature is a maximum value and the SV of the intestinal signature is a minimum value is determined as an inflammatory molecular subtype; among clusters except for the cluster determined as the gastric molecular subtype, the cluster determined as the mesenchymal molecular subtype, and the cluster determined as the inflammatory molecular subtype, a cluster in which the SV of the stem-like signature is a maximum value is determined as a mixed-stromal molecular subtype; and the last remaining cluster is determined as an intestinal molecular subtype.

A prognosis for each classified molecular subtype is predicted in terms of overall survival based on a survival curve of the molecular subtype.

The molecular subtypes of gastric cancer exhibit differentiated prognostic patterns as observed in the survival curves, and in terms of overall survival, the inflammatory molecular subtype may be predicted as a good prognosis group, the intestinal and gastric molecular subtypes may be predicted as intermediate prognosis group, and the mixed-stromal and mesenchymal molecular subtypes may be predicted as bad prognosis group.

Thus, by determining a molecular subtype to which the biological sample belongs and examining a survival curve of the molecular subtype, a prognosis may be predicted.

The biological sample may be fresh tumor tissue, fresh-frozen tumor tissue, formalin fixed paraffin-embedded tumor tissue, a fine needle aspirate, ascites, a tube washing solution, a pleural fluid, or the like, and is preferably formalin-fixed paraffin-embedded tumor tissue.

In addition, the measuring of the mRNA expression level of the target gene group may be performed by qPCR.

Advantages and features of the present invention, and methods of achieving the same will become apparent with reference to the following examples. The present invention may, however, be embodied in many different forms and should not be construed as being limited to the examples set forth herein. Rather, these examples are provided so that this invention will be thorough and complete, and will fully convey the scope of the invention to those of ordinary skill in the art to which the present invention pertains, and the present invention is defined merely by the scope of the appended claims.

EXAMPLES (Patients and Samples)

Fresh-frozen tumor specimens and clinical data of gastric cancer patients who underwent gastric cancer resection during primary treatment at Yonsei University Severance Hospital (YUSH) from 2000 to 2010 were acquired. All samples were collected after obtaining written consent from the patients, and the study was approved by the Institutional Review Committee of YUSH. The samples were annotated but were separated from patient-identifiable information. Clinical data was obtained retrospectively. Overall survival (OS) was defined with respect to the time from surgery to death, and recurrence-free survival was defined with respect to the time from surgery to the first recurrence. Data was censored when a patient was alive without recurrence at the time of the last contact.

Gene expression profiles of 497 samples of surgically removed frozen GC tumor tissue were obtained using the HumanHT-12 v3.0 Expression BeadChip array (Illumina) with 48,803 gene characteristics (GSE13861p). Briefly, total RNA was extracted from fresh-frozen tissue using a RecoverAll™ total nucleic acid isolation kit (Ambion) or a mirVana RNA isolation labeling kit (Ambion). RNA concentration and purity were measured at 260 nm and 280 nm ($A_{260}$:$A_{280}$=1.8) using a NanoDrop 2000 (Thermo Fischer Scientific). The integrity of the RNA was evaluated using an RNA Nano 6000 chip (Agilent) (RIN>7). 500 ng of total RNA was labeled in accordance with the manufacturer's protocols using a TotalPrep™ RNA amplification kit (Illumina), and then gene expression levels were measured using the BeadChip array platform.

(Training Sets and Test Sets for GC Learning)

The Training set I for finding GC molecular subtypes consisted of GSE13861p (n=497, Illumina HumanHT-12 v3.0 Expression BeadChip array). The Test set I for confirming the GC molecular subtypes consisted of data sets of GSE15459 (n=200, Affymetrix Human Genome U133plus 2.0 Array), TCGA (n=262, Illumina HiSeq2000), and GSE62254 (n=300, Affymetrix Human Genome U133plus 2.0 Array).

To select the final miniClassifier-26 (26 genes), the Training set II consisted of Merged1259 (n=1259) obtained by combining GSE13861p (n=497), GSE15459 (n=200), TCGA (n=262), and GSE62254 (n=300) using the ComBat method, and qPCR-based, measurable 26 genes were identified by the Test set II consisting of qPCR325 (n=325). To obtain qPCR325, total RNA was extracted using the MasterPure™ Complete DNA and RNA Purification Kit (Epicentre). cDNA was produced using M-MLV Reverse Transcriptase (Life Technologies). The concentration of cDNA was determined using NanoDrop 2000. qPCR was performed using the SensiFAST Probe Lo-ROX Kit (Bioline), 5'FAM/3'BHQ-1 Probe (Biosearch Technologies), gene-specific primers, and ViiA™ 7 Real-Time PCR System (Applied Biosystems), and 5 ng of total cDNA.

(Data Processing)

Data pre-processing: Microarray data sets were mainly processed in the R language environment. Normalization was performed by Between-Array Normalization (quantile) in the "Linear Models for Microarray Data (limma)" for data sets from the Illumina BeadChip array platform. GSE 15459 and GSE62254 were normalized using the R "affy" package including Robust Multi-array Average normalization. qPCR data sets were normalized by internal standards. For gene filtering, platform-derived probe validity and variance in gene expression should be considered. In the case of the training sets, data sets were adjusted by batch adjustment and then combined with the method "Combatting Batch Effects When Combining Batches of Gene Expression Microarray Data (ComBat)".

NMF-based classification: The ComBat-merged data was classified using the package "Algorithm and Framework for Nonnegative Matrix Factorization (NMF)". The number of clusters (k) was set from 2 to 7. The Brunet method was used as an updating algorithm for iterative approximation. Before characterizing NMF-derived clusters, outlier samples were excluded from each cluster by using the "Silhouette" R package. To define genes representing each NMF cluster, SAM and PAM were performed using the Bioconductor packages "siggenes" and "pamr," respectively.

WGCNA analysis: The WGCNA was performed with respect to 497 GC samples, using the R "wgcna" package. For network construction, weighted network adjacency was defined by co-expression similarity with a power of 6. To avoid choosing an arbitrary cut-off, the "soft-thresholding procedure" provided by WGCNA was used. Dynamic hybridization from the R "dynamicTreeCut" package was applied as a module-detection method. To evaluate whether each module was associated with survival and clinicopathological variables, various module characteristics such as connectivity, module significance, and module eigengene were utilized.

Gene set enrichment analysis (GSEA): The GSEA was performed using the R "GSEABase" package. A priori-defined sets of genes were available from Molecular Signatures Database (MSigDB; www(dot)broadinstitute(dot)org/msigdb). Enrichment analysis was performed using gene ontology from the Gene Ontology Consortium (www(dot)geneontology(dot)org).

Survival analysis: The survival analysis was performed using the Cox proportional hazard model and meta-analysis of HR in the R "survival" and "meta" packages, respectively.

Hierarchical clustering and illustration of gene expression profiles: The gene clustering of microarray data sets was performed using Gene Cluster 3.0. Hierarchical clustering results were graphically visualized using the R "gplots" package.

(Statistical Analysis)

The hypergeometric test/Fisher's exact test, Pearson's correlation, Spearman's correlation, and the Wilcoxon rank-sum test were performed as statistical tests.

(Primary Cell-Specific Gene Expression Profiling)

Primary cell culture: Primary tissue was rinsed with Dulbecco's phosphate-buffered saline (Welgene LB00-02) containing 2% antibiotics (Welgene LS203-01) and minced with a sterile blade. After 0.2-μm syringe filtration, the minced tissue was incubated with α-MEM (Gibco A10490) and 150 U/ml Collagenase II (Thermo Fisher Scientific) at 37° C. in a humidified atmosphere with 5% $CO_2$ for 24 hours. The cultured tissue was centrifuged at 200×g for 5 minutes and then transferred to a fresh medium. The harvested cells were cultured at 37° C. under a 5% $CO_2$ atmosphere for 2 days to 3 days.

Total RNA sequencing using Illumina HiSeq 2500 sequencing system: RNA purity was determined by analyzing 1 μl of a total RNA extract on a NanoDrop8000 spectrophotometer. Total RNA integrity was verified using an Agilent Technologies 2100 Bioanalyzer with an RNA integrity number (RIN) value and the percentage of RNA fragments>200 nt fragment distribution value (DV200). Total RNA sequencing library was prepared in accordance with the manufacturer's instructions (Illumina TruSeq RNA Access Library kit). Subsequently, 100 ng of total RNA was fragmented into small pieces using divalent cations at a high temperature. cDNA was generated from the cleaved RNA fragments using random priming during first and second strand synthesis, and sequencing adapters were ligated to the resulting double-stranded cDNA fragments. The coding regions of the transcriptome were captured from this library using sequence-specific probes to generate the final library. The quality of the amplified libraries was verified by capillary electrophoresis (Bioanalyzer, Agilent). qPCR was performed using the SYBR Green PCR Master Mix (Applied Biosystems), and then libraries index tagged in equimolar amounts were combined in a pool. Cluster generation was realized in the flow cell on the cBot automated cluster generation system (Illumina). Subsequently, the flow cell was loaded onto a HiSeq 2500 sequencing system (Illumina) and sequence analysis was performed using a read length of 2×100 bp.

(In Vitro and In Vivo Experimental Validation)

Cell lines: Human gastric cancer cell lines SNU-1, SNU-5, SNU-16, SNU-216, SNU-484, SNU-520, SNU-601, SNU-620, SNU-638, SNU-668, SNU-719, MKN-1, MKN-45, MKN-74, KATOIII, NCI-N87, and Hs746T were purchased from the Korean Cell Line Bank (Seoul, Korea); and YCC-1, YCC-2, YCC-3, YCC-6, YCC-7, YCC-9, YCC-10, YCC-11, and YCC-16 were purchased from the Yonsei Cancer Research Institute (Seoul, Korea). SNU-1, SNU-5, SNU-16, SNU-216, SNU-484, SNU-520, SNU-601, SNU-620, SNU-638, SNU-668, SNU-719, MKN-28, MKN-45, MKN-74, KATOIII, and NCI-N87 were grown in RPMI 1640 (Welgene, Daegu, Korea); Hs746T was grown in Dulbecco's modified Eagle's medium (DMEM; Welgene, Daegu, Korea); and YCC-1, YCC-2, YCC-3, YCC-6, YCC-7, YCC-9, YCC-10, YCC-11, and YCC-16 were grown in Minimum essential media Eagle (MEM; Welgene, Daegu, Korea). All cells were cultured at 37° C. in a complete medium supplemented with 10% FBS (Gibco) and 1% antibiotic-antimicrobial solution (containing 10,000 units of penicillin, 10 mg of streptomycin, and 25 μg of amphotericin B/mL, Sigma-Aldrich) in a 5% $CO_2$-containing humidified atmosphere. All cells were confirmed negative for mycoplasma by e-Myco™ and Mycoplasma PCR Detection Kit (iNtRON Biotechnology, Seongnam, Korea).

Invasion assay: For the assay, 2×10⁴ HUVEC cells were placed in a culture medium (M199) in a fibronectin-coated transwell, followed by coating the bottom of the transwell with 0.2% gelatin and cell culture for 48 hours until monolayer formation. Thereafter, 1×10⁵/50 μl Hs746T and NCI-N87 cells containing FBS-free CellTracker™ (Molecular Probes, C2925) were separately added to the transwell. A culture medium containing 10% FBS was added to the lower chamber. After incubation for 48 hours, upper cells of the membrane were removed using a cotton swab. Cells on the lower membrane were lysed in 200 μl of a lysis buffer at room temperature for 2 hours to 3 hours. Fluorescence was measured with Ex/Em 492/517. To examine the effect of a TGF-β inhibitor on cell invasion ability, 50 μM of LY2157299 (AdooQ, California, USA) was administered.

Migration assay: Hs746T and NCI-N87 cells were grown into monolayers in a culture medium containing 10% FBS and 1% antibiotics. When confluency reached 70%, the cell monolayers were scratched with a 100-μl pipette tip. After 72 hours, the wound width was measured and normalized by the wound width measured immediately after scratching. LY2157299 (50 μM) was administered to evaluate the effect of the TGF-β inhibitor on cell migration.

Tumor spheroid formation assay: Ten cells were cultured in 50 μl of DMEM/F12 (Gibco) supplemented with bFGF, EGF, B27, 10% FBS, and 1% antibiotics in a 96-well plate. After 30 days of cell culture, the number of tumor spheroids in each well was counted. In addition, LY2157299 (50 μM)

was administered to examine the effect of the TGF-β inhibitor on tumor sphere formation.

In vivo tumorigenesis in orthotopic mouse model: All animal experiments were conducted with the approval of the Association for Assessment and Accreditation of Laboratory Animal Care (AAALAC) International. To establish an orthotopic xenograft mouse model, the skin and the peritoneum of each of BALB/c nude mice (male) were incised along the upper midline by approximately 5 mm for about 1 hour, and 1×10$^7$ GC cells (Hs746T and NCI-N87) were transplanted into the exteriorized gastric wall of each mouse. The stomach was returned to the peritoneum and the abdominal wall was closed with one layer of wound suture. To observe tumor growth in the model, the presence and size of cancer were monitored using a 9.4 T animal magnetic resonance imaging (MRI) instrument equipped with a Bruker animal coil (RF SUC 400 1H M-BR-LIN ROAD, Bruker Medical Systems) (MRI measurement conditions: Echo=1, TR=2300 ms, TE=22.0 ms, FA=180 deg, TA=0h4m54s400 ms, NEX=2, and FOV=4.00 cm).

Drug response in xenograft mouse model: To establish a xenograft mouse model, 1×10$^7$ GC cells (Hs746T and NCI-N87) were transplanted into the proximal femoral region of each of BALB/c nude mice (male). When the tumor volume increased to 400 mm$^3$, tumor-bearing mice were randomized into three different treatment groups (PBS control, Oxal+5FU/PBS-treated group, and Oxal+5FU/LY2157299 (TBF-β inhibitor)-treated group, n=8 per group). Oxalipatin (60 μg per single dose) and Fluorourasil (1 mg per single dose) were mixed and the resulting mixture was intraperitoneally injected into each mouse three times a week. LY2157299 (1.5 mg/mouse) was administered twice a week to an intra-tumor injection model. The size of the transplanted tumor was examined three times per week and calculated by (4/3)×π×(minor axis/2)$^2$×(major axis/2) mm$^3$.

Heterogeneity testing of miniClassifier-26 for qPCR analysis: To examine the possibility of spatial heterogeneity affecting the procedure of the present invention for preparing tissue samples from an FFPE specimen, three tissue samples were obtained from a single FFPE specimen for RNA extraction. After cDNA was prepared, qPCR was performed three times and an average of each of the three samples derived from the single tumor specimen was obtained. The heterogeneity across the three samples was determined by evaluating the coefficient of variance for each gene.

(Tissue Microarray Construction)

Two representative 3-mm-diameter tumor tissue cores in each formalin-fixed paraffin-embedded primary tumor were assembled into tissue microarray (TMA) blocks. Each TMA block contained 14 tumors and one normal gastric mucosal tissue core as markers and internal controls. Subsequently, for immunohistochemistry (IHC) analysis, 4-μm-thick sections were prepared from each TMA block.

(Immunohistochemistry (IHC))

The IHC was performed as described above using a Ventana XT system (Ventana Corporation) with antibodies for MutL homolog 1 (MLH1, ready to use, Roche, Basel, Switzerland), MutS protein homolog 2 (MSH2, ready to use, clone G219-1129). In the case of MLH1 and MSH2, the absence of nuclear staining in tumor cells was defined as loss of expression, and normal expression was defined as the presence of nuclear expression in tumor cells. All IHC results were evaluated without knowledge of clinical pathological characteristics.

(Epstein-Barr Virus-Encoded RNA In-Situ Hybridization (EBER ISH))

The EBER ISH was performed using a Ventana Bench Mark system (ISH iView kit, Ventana Corporation, AZ, USA). Formalin-fixed paraffin-embedded tissue sections were deparaffinized with EZ Prep buffer (Ventana Corporation) and digested with protease I for 4 minutes. Subsequently, probes for EBER were denatured at 85° C. for 10 minutes and then hybridized at 37° C. for 1 hour. After hybridization, the tissue was washed with 2×SSC buffer at 57° C. Subsequently, incubation with an anti-fluorescein monoclonal antibody was performed for 20 minutes, and then an Alkaline Blue detection kit (Ventana Corporation) was used in accordance with the manufacturer's protocol. Slides were counterstained with Nuclear Fast Red for 10 minutes.

TABLE 1

List for target gene group and reference gene group, primer sets and probes

| No. | Gene name | Primer No. | Accession No. | Product size | start | stop | | Primer/Probe sequence (SEQ ID NO.)(5'-3') |
|---|---|---|---|---|---|---|---|---|
| 1 | TFF1 | N643-2 | NM_003225 | 75 | 196 | 270 | Forward primer | aaataagggctgc tgtttcg (SEQ ID NO: 1) |
| | | | | | | | Reverse primer | gggacgtcgatgg tattagg (SEQ ID NO: 2) |
| | | | | | | | Probe | acgacaccgttcg tggggtc (SEQ ID NO: 63) |
| 2 | TFF2 | N644-2 | NM_005423 | 67 | 357 | 423 | Forward primer | ccctcccaaagca agagtc (SEQ ID NO: 3) |
| | | | | | | | Reverse primer | gggtagccacagt ttcttcg (SEQ ID NO: 4) |
| | | | | | | | Probe | tcagtgcgtcatgg aggtctca (SEQ ID NO: 64) |

TABLE 1-continued

List for target gene group and reference gene group, primer sets and probes

| No. | Gene name | Primer No. | Accession No. | Product size | start | stop | | Primer/Probe sequence (SEQ ID NO.)(5'-3') |
|---|---|---|---|---|---|---|---|---|
| 3 | VSIG1 | N649-1 | NM_001170553 | 64 | 812 | 875 | Forward primer | catcgtgccagtg aaagaaa (SEQ ID NO: 5) |
| | | | | | | | Reverse primer | tgtcagatttccaat gaccaa (SEQ ID NO: 6) |
| | | | | | | | Probe | tcaacccaaccac cgggatt (SEQ ID NO: 65) |
| 4 | CNN1 | N185-5 | NM_001299.4 | 68 | 526 | 593 | Forward primer | agtccaccctcctg gcttt (SEQ ID NO: 7) |
| | | | | | | | Reverse primer | cttcactcccacgt tcacctt (SEQ ID NO: 8) |
| | | | | | | | Probe | cctttcgtct tcgccatgct gg (SEQ ID NO: 66) |
| 5 | NEXN | N797-3 | NM_144573.3 | 66 | 1152 | 1217 | Forward primer | gcggcaaatggta aatgaag (SEQ ID NO: 9) |
| | | | | | | | Reverse primer | gggcggtacccttt aaaaat (SEQ ID NO: 10) |
| | | | | | | | Probe | tgaggaaaaccaa gacacagcaaa (SEQ ID NO: 67) |
| 6 | SCRG1 | N710-2 | NM_007281.2 | 72 | 338 | 409 | Forward primer | cccagtgagtgtg agcattt (SEQ ID NO: 11) |
| | | | | | | | Reverse primer | gcttttggcccttttt cttc (SEQ ID NO: 12) |
| | | | | | | | Probe | tggtcttggcaga ggatgcttc (SEQ ID NO: 68) |
| 7 | SORBS1 | N835-3 | NM_015385.3 | 75 | 263 | 337 | Forward primer | gctgtgatgaatg gcttgg (SEQ ID NO: 13) |
| | | | | | | | Reverse primer | cccagtgcagattt ttgtagg (SEQ ID NO: 14) |
| | | | | | | | Probe | ttgtcttgcccattg ctgcc (SEQ ID NO: 69) |
| 8 | SPARCL1 | N454-3 | NM_004684.2 | 69 | 401 | 469 | Forward primer | cattccaaaccaa ctgctga (SEQ ID NO: 15) |
| | | | | | | | Reverse primer | agcttcagcccata aactgg (SEQ ID NO: 16) |
| | | | | | | | Probe | cggtagcacctga caacactgc (SEQ ID NO: 70) |
| 9 | AURKA | N471-2 | NM_198434.1 | 69 | 1074 | 1142 | Forward primer | gcagattttgggtg gtcagt (SEQ ID NO: 17) |
| | | | | | | | Reverse primer | gtagtccagggtg ccacaga (SEQ ID NO: 18) |
| | | | | | | | Probe | ctccatcttccagg aggacca (SEQ ID NO: 71) |

TABLE 1-continued

List for target gene group and reference gene group, primer sets and probes

| No. | Gene name | Primer No. | Accession No. | Product size | start | stop | | Primer/Probe sequence (SEQ ID NO.)(5'-3') |
|---|---|---|---|---|---|---|---|---|
| 10 | BUB1 | N245-1 | NM_004336.2 | 75 | 1776 | 1850 | Forward primer | ccttcaaaaccaa aggagga (SEQ ID NO: 19) |
| | | | | | | | Reverse primer | gcagcgaataccc cataca (SEQ ID NO: 20) |
| | | | | | | | Probe | ccaaaaactc ttcagcatga ggca (SEQ ID NO: 72) |
| 11 | CDC20 | N504-3 | NM_001255 | 71 | 607 | 677 | Forward primer | cttccctgccagac cgtat (SEQ ID NO: 21) |
| | | | | | | | Reverse primer | ccaatccacaagg ttcaggt (SEQ ID NO: 22) |
| | | | | | | | Probe | cctggatgcgcct gaaatcc (SEQ ID NO: 73) |
| 12 | CEP55 | N731-2 | NM_018131.4 | 74 | 438 | 511 | Forward primer | caagtgggaaag gaaagctg (SEQ ID NO: 23) |
| | | | | | | | Reverse primer | ctcagcctcaagg actcgaa (SEQ ID NO: 24) |
| | | | | | | | Probe | ttttctccaaaagtc tgtgtctctc (SEQ ID NO: 74) |
| 13 | PTTG1 | N813-2 | NM_004219.3 | 67 | 166 | 232 | Forward primer | ctgaagctggggt ctgga (SEQ ID NO: 25) |
| | | | | | | | Reverse primer | aacgtggtgttgaa acttgaga (SEQ ID NO: 26) |
| | | | | | | | Probe | ccttcaatcaaagc cttagatggga (SEQ ID NO: 75) |
| 14 | UBE2C | N716-3 | NM_181802.1 | 73 | 1021 | 1093 | Forward primer | ccctgctatcaccc caac (SEQ ID NO: 27) |
| | | | | | | | Reverse primer | gggcagaccactt ttccttc (SEQ ID NO: 28) |
| | | | | | | | Probe | cacccagggtaac atatgcctgg (SEQ ID NO: 76) |
| 15 | CD8A | N205-5 | NM_171827.3 | 70 | 1745 | 1814 | Forward primer | cagagctacccgc agagttc (SEQ ID NO: 29) |
| | | | | | | | Reverse primer | aagaggttgagat ggcatgg (SEQ ID NO: 30) |
| | | | | | | | Probe | tgcctccagct ctctcagcat ga (SEQ ID NO: 77) |

TABLE 2

| No. | Gene name | Primer No. | Accession No. | Product size | start | stop | | Primer/Probe sequence (SEQ ID NO.) |
|---|---|---|---|---|---|---|---|---|
| 16 | GBP1 | N699-3 | NM_002053 | 73 | 163 | 235 | Forward primer | tagaagccagtg ctcgtgaa (SEQ ID NO: 31) |
| | | | | | | | Reverse primer | gatctctgatgcc atgtcca (SEQ ID NO: 32) |

TABLE 2-continued

| No. | Gene name | Primer No. | Accession No. | Product size | start | stop | | Primer/Probe sequence (SEQ ID NO.) |
|---|---|---|---|---|---|---|---|---|
| | | | | | | | Probe | agaaaagaac agacaagggaa cagcc (SEQ ID NO: 78) |
| 17 | GBP5 | N700-1 | NM_052942 | 69 | 835 | 903 | Forward primer | ggcctgggagat gtagagaa (SEQ ID NO: 33) |
| | | | | | | | Reverse primer | cagtaagagtgc cagtgcaaa (SEQ ID NO: 34) |
| | | | | | | | Probe | tctggatatcattc ttgttgtcagcc (SEQ ID NO: 79) |
| 18 | GZMB | N464-1 | NM_004131.3 | 65 | 213 | 277 | Forward primer | cggtggcttcctg atacaag (SEQ ID NO: 35) |
| | | | | | | | Reverse primer | ttatggagcttcc ccaacag (SEQ ID NO: 36) |
| | | | | | | | Probe | cgacttcgtgctg acagctgc (SEQ ID NO: 80) |
| 19 | NKG7 | N705-2 | NM_005601.3 | 66 | 641 | 706 | Forward primer | gtccccgtcctg gctatg (SEQ ID NO: 37) |
| | | | | | | | Reverse primer | aacgctcaaaac tcatcttgc (SEQ ID NO: 38) |
| | | | | | | | Probe | cgctcttgccttct gctcaca (SEQ ID NO: 81) |
| 20 | WARS | N717-3 | NM_173701.1 | 73 | 408 | 480 | Forward primer | ttgtggacccatg gacagta (SEQ ID NO: 39) |
| | | | | | | | Reverse primer | ccaaaccgaaca atgagctt (SEQ ID NO: 40) |
| | | | | | | | Probe | tgccttttgcactg cttgtctg (SEQ ID NO: 82) |
| 21 | ANTXR1 | N722-2 | NM_053034.2 | 67 | 558 | 624 | Forward primer | cagttggctcac aaattcatc (SEQ ID NO: 41) |
| | | | | | | | Reverse primer | ttcctcgggtgga gaaaac (SEQ ID NO: 42) |
| | | | | | | | Probe | aaaggacattctc aactgtgggc (SEQ ID NO: 83) |
| 22 | SFRP4 | N187-3 | NM_003014.2 | 64 | 1298 | 1361 | Forward primer | ggagacttccga cttccttaca (SEQ ID NO: 43) |
| | | | | | | | Reverse primer | tggccttacatag gctgtcc (SEQ ID NO: 44) |
| | | | | | | | Probe | aggcaatgcc cagcctcatc (SEQ ID NO: 84) |
| 23 | VCAN | N595-3 | NM_001126336 | 74 | 1830 | 1903 | Forward primer | tttgagcatgactt ccgttg (SEQ ID NO: 45) |
| | | | | | | | Reverse primer | ctgtctggctggt tgggtct (SEQ ID NO: 46) |
| | | | | | | | Probe | tggcagcacact gcaatacga (SEQ ID NO: 85) |

TABLE 2-continued

| No. | Gene name | Primer No. | Accession No. | Product size | start | stop | | Primer/Probe sequence (SEQ ID NO.) |
|---|---|---|---|---|---|---|---|---|
| 24 | CDH17 | N729-3 | NM_004063.3 | 68 | 1882 | 1949 | Forward primer | gcaatgtgactg ccaaggat (SEQ ID NO: 47) |
| | | | | | | | Reverse primer | acctcttgtgtctc ccctca (SEQ ID NO: 48) |
| | | | | | | | Probe | ccagaaggtctg gacataagc (SEQ ID NO: 86) |
| 25 | CDX1 | N730-2 | NM 001804.2 | 67 | 1319 | 1385 | Forward primer | agggaggaacg tggtcaact (SEQ ID NO: 49) |
| | | | | | | | Reverse primer | tatgatggggc aggtagaa (SEQ ID NO: 50) |
| | | | | | | | Probe | tgcctcttcctgc agcctca (SEQ ID NO: 87) |
| 26 | MYO1A | N793-3 | NM_005379.3 | 71 | 1034 | 1374 | Forward primer | ccgcctctttgac tggatag (SEQ ID NO: 51) |
| | | | | | | | Reverse primer | ccttcttcttttccc cgatg (SEQ ID NO: 52) |
| | | | | | | | Probe | cccaccttgatgc tctcattgattc (SEQ ID NO: 88) |
| 27 | ACTB | N037 | NM_001101 | 72 | 278 | 349 | Forward primer | tcaccctgaagta ccccatc (SEQ ID NO: 53) |
| | | | | | | | Reverse primer | tgtggtgccagat tttctcc (SEQ ID NO: 54) |
| | | | | | | | Probe | cggcatcgtcac caactggg (SEQ ID NO: 89) |
| 28 | ATP5E | N041 | NM_006886 | 74 | 117 | 189 | Forward primer | atggtggcctact ggagaca (SEQ ID NO: 55) |
| | | | | | | | Reverse primer | Ctctcactgctttt gcacaga (SEQ ID NO: 56) |
| | | | | | | | Probe | tggactcagcta catccgatactcc ca (SEQ ID NO: 90) |
| 29 | GPX1 | N201-5 | NM_000581.2 | 71 | 308 | 378 | Forward primer | cccgtgcaacca gtttgg (SEQ ID NO: 57) |
| | | | | | | | Reverse primer | ggacgtacttga gggaattcaga (SEQ ID NO: 58) |
| | | | | | | | Probe | ctcttcgttcttgg cgttct cctgatg (SEQ ID NO: 91) |
| 30 | UBB | N203-5 | NM_018955.2 | 78 | 61 | 138 | Forward primer | tgggtgagcttgt ttgtgtc (SEQ ID NO: 59) |
| | | | | | | | Reverse primer | tttgacctgttagc ggatacc (SEQ ID NO: 60) |
| | | | | | | | Probe | caccaaccacgt ccacccac (SEQ ID NO: 92) |

TABLE 2-continued

| No. | Gene name | Primer No. | Accession No. | Product size | start | stop | Primer/Probe sequence (SEQ ID NO.) | |
|---|---|---|---|---|---|---|---|---|
| 31 | HPRT1 | N049-2 | NM_000194.1 | 67 | 531 | 597 | Forward primer | tggtcaggcagt ataatccaa (SEQ ID NO: 61) |
|  |  |  |  |  |  |  | Reverse primer | cttcgtggggtcc ttttcac (SEQ ID NO: 62) |
|  |  |  |  |  |  |  | Probe | tgcaagcttgc gaccttgacc (SEQ ID NO: 93) |

<Example 1> Classification of Advanced Gastric Cancer into Five Types

An experimental flowchart of the present invention is provided in FIG. 1. The inventors of the present invention identified five GC molecular subtypes based on consensus-based NMF. The inventors of the present invention investigated gene expression profiles of gastrectomy samples (n=497) from patients with GC (GSE13861p Training set I; HumanHT-12 v3.0 Array (Illumina)). The classification of GC for the five molecular subtypes showed high consensus, and heatmaps showed a distinct gene expression pattern (see FIGS. 2A and 3). The inventors of the present invention identified 932 subtype-specific genes (Classifier-PAM932) using a prediction analysis of microarrays (PAM; overall error rate=0.10) following significance analysis of microarrays (SAM, false discovery rate (FDR)=0). Classifier-PAM932 was used to stably identify subtypes in independent gene expression data sets (Test set I) of GC patients.

<Example 2> Identification of Six Molecular Signatures Describing GC Subtypes

To extend the denotation of a priori-defined gene sets, additional unsupervised gene-wise clustering was performed. In GSE13861p, the WGCNA detected 32 gene modules (clusters of highly interconnected genes) (see FIG. 4 (upper view and middle view)). Overall, it was observed that (i) several modules were significantly conserved across cohorts (hypergeometric test; P<0.01) (see FIG. 4A (middle view)), (ii) the conserved modules were due to a relative difference in PAM analysis of the top 25% of PAMgenes (see FIG. 4A (lower view)), and (iii) these associations were significantly relevant to GC biology (see FIG. 4A (lowest view)). Six GC signatures were remarkably associated with five GC subtypes, based on the conserved modules. The inventors of the present invention re-extracted genes of the GC signatures and showed that a particular combination of the GC signatures could be translated to five NMF-derived subtypes using Spearman's correlation (see FIG. 4B). Annotation of the five subtypes by the inventors of the present invention is more biologically relevant by the characterization of subtypes based on the network analysis.

<Example 3> Clinical Characterization of Five GC Subtypes

Figure 5:
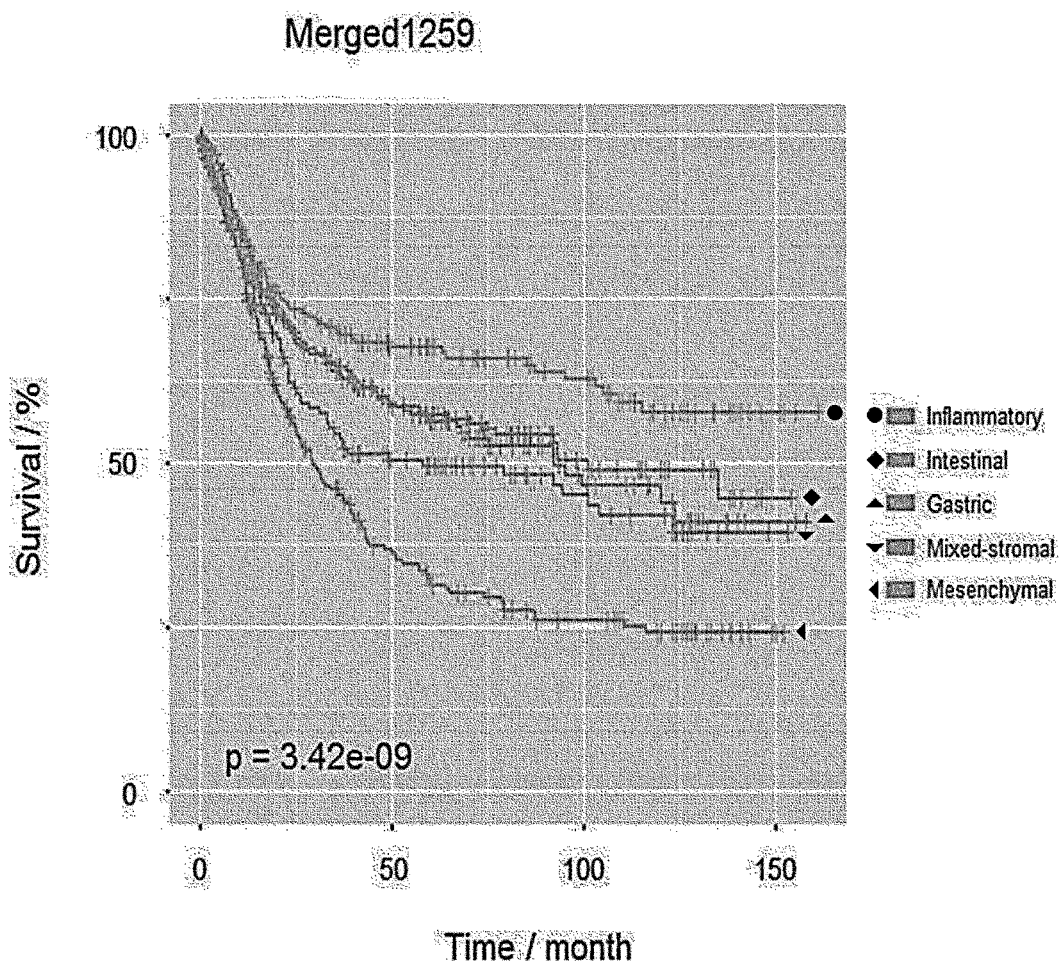
FIG. 5 illustrates an overall survival (OS) rate according to five subtypes by using Merged1259 (GSE13861p, GSE62254 (ACRG), TCGA, and GSE15459 (Singapore)), which is the training set of process II (likelihood ratio test; p=3.42e-09), and illustrates overall survival curves of 1198 samples, except for 61 samples with no clinical information, among Merged1259 cohort samples, wherein the five-year survival rate of each molecular subtype is 76.1% for INF (95% confidence interval, 67.7-85.7), 65.1% for INT (95% confidence interval: 56.2-75.4), 64.6% for GST (95% confidence interval: 55.0-75.9), 51.3% for MXD (95% confidence interval: 42.1-62.4), and 46.3% for MSC (95% confidence interval: 38.0-56.5).

The relationship between GC subtypes and clinicopathological information (age, sex, tumor location, AJCC stage ($6^{th}$), WHO classification, and Lauren type) was examined. For the survival analysis of five subtypes, a significant association between subtypes and overall survival was examined (P=3.42e-09, see FIG. 5). The five-year survival rate of each subtype was determined: 76.1% for INF (95% confidence interval: 67.7-85.7), 65.1% for INT (95% confidence interval: 56.2-75.4), 64.6% for GST (95% confidence interval: 55.0-75.9), 51.3% for MXD (95% confidence interval: 42.1-62.4), and 46.3% for MSC (95% confidence interval: 38.0-56.5). The INF subtype was associated with a significantly lower risk of death than the MXD and MSC subtypes in the Training set I.

Finally, similarities and differences of the classification were compared with the GC subtypings reported by the Asian Cancer Research Group (ACRG) (GSE62254), the Cancer Genome Atlas (TCGA), and the Singapore Research Group (GSE15459): that is, i) the MSC subtype showing the worst clinical outcome was a consensus subtype across the four classification systems including the ACRG EMT subtype, the TCGA GS subtype, and the Singapore research group invasive subtype; and ii) in the INF subtype with the best clinical outcome, most Epstein-Barr virus (EBV)-positive patients and a partial high-microsatellite instability (MSI) group identified by TCGA and ACRG were included. Otherwise, the GST and INT subtypes were partially described by the Singapore research group. The MXD subtype was associated with structural chromosomal instability by TCGA. Subtype matching tended to be pathologically ambiguous in non-MSC and non-INF GC population, probably because TCGA and ACRG used somatic copy number and the degree of TP53 activity as classifiers.

Figure 6A:
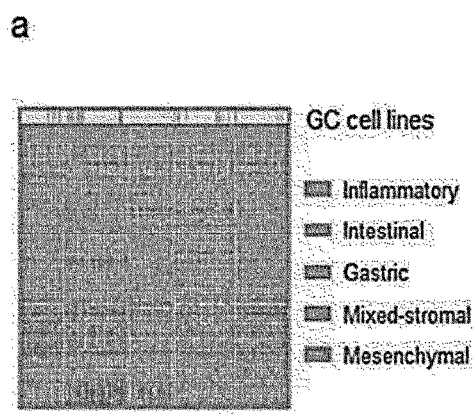
Figure 6B:
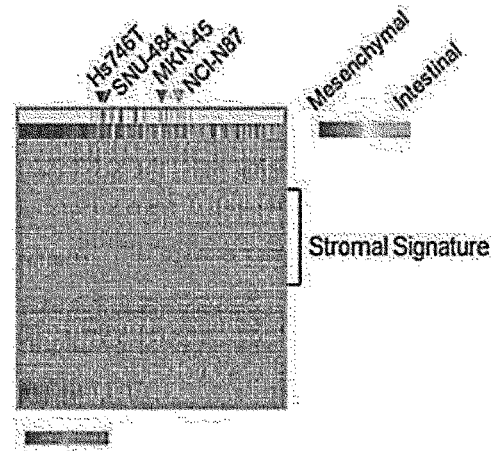

<Example 4> Preclinical Therapeutic Response of MSC Subtype Compared to INT Subtype In the module stromal analysis, the stromal signature was significantly associated with the diffuse type, as well as with recurrence, in Lauren classification. This prompted the verification of mesenchymal and stem-like behaviors of the MSC subtype using GC cell lines. Furthermore, as recent evidences have shown that the acquisition of EMT-associated drug resistance leads to poor prognosis in various types of cancer, the preclinical therapeutic response of the MSC subtype was evaluated. GC cell lines (n=26) were classified into five subtypes after merging the gene expression data on cell lines with data on patient GC tumor samples (distance-weighted discrimination method) (see FIG. 6A). By ranking with stromal module eigengene, the Hs746T and SNU484 GC cell lines were selected as model cell lines from the MSC-subtyped cell lines. NCI-N87 and MKN-45 cells, assigned to the INT subtype, were used as a control with no stromal signature (see FIG. 6B). In in vitro invasion and wound-healing assays, Hs746T and SNU484 cells exhibited greater invasive performance and mobility than NCI-N87 and MKN-45 cells (see FIGS. 7A and 7B). According to the result of 3D spheroid formation assay, the Hs746T and SNU484 cells exhibited stem-like characteristics (see FIG. 7C). T2-weighted axial magnetic resonance images of an in vivo orthotopic tumor model revealed that, while the NCI-N87 and MKN-45 cells formed confined tumors, Hs746T and SNU484 tumors diffused along the gastric wall (see FIG. 7E, white dotted line). In addition, the effect of a TGF-β inhibitor (LY2157299) on the stromal characteristics of Hs746T compared to the NCI-N87 cells was observed. Treatment with a TGF-β inhibitor delayed the wound-healing, invasion, and 3D spheroid formation abilities of Hs746T cells in vitro (see FIGS. 7E to 7G). To confirm EMT-involved drug resistance, the TGF-β inhibitor and chemotherapy combination (oxaliplatin+5-FU) were co-administered to an in vivo xenograft mouse model established using Hs746T cells. Although the oxaliplatin+5-FU treatment was only marginally effective against tumor growth in the Hs746T model, the co-administration of TGF-β inhibitor and oxaliplatin+5-FU significantly reduced the drug resistance and volume of tumors in Hs746T (see FIG. 7H). On the other hand, the chemotherapy combination alone reduced tumor growth in non-stromal NCI-N87 tumors without the aid of the TGF-β inhibitor (see FIG. 7I).

<Example 5> GC miniClassifier-26 as qPCR Probe Set for Clinical Application

Figure 9:
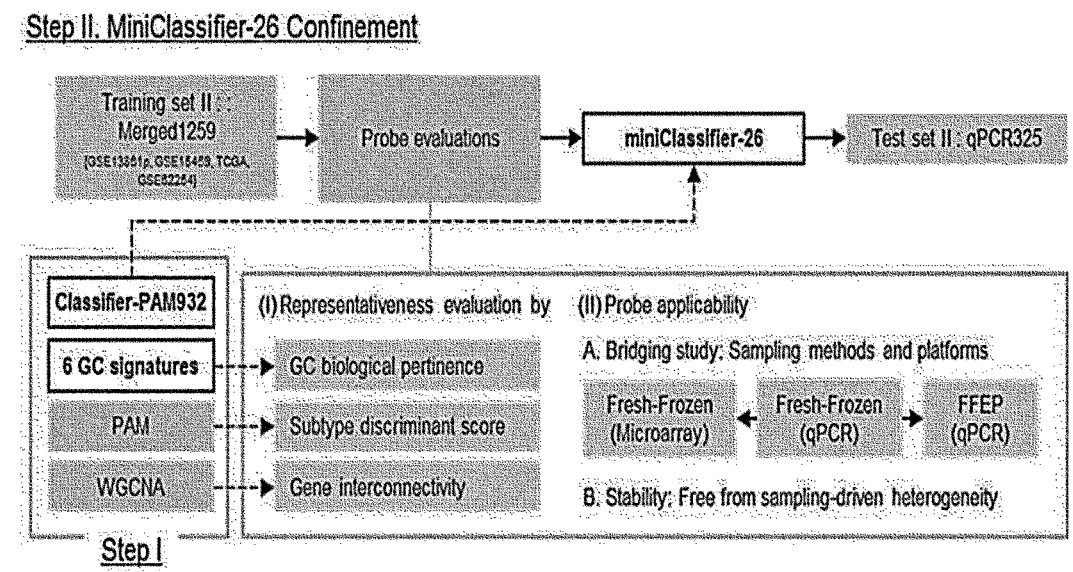
FIG. 9 is a detailed flowchart illustrating the selection and analysis of 26 genes with stability (miniClassifier-26) from microarray data and qPCR data of fresh-frozen tissue and qPCR data of formalin fixed paraffin-embedded samples.

Classifier-PAM932 was refined into miniClassifier-26 as a qPCR probe set to establish a robust and clinically utilizable classification system (see FIG. 8) (FIG. 9 is a flowchart illustrating the selection and analysis of miniClassifier-26). For classifier selection, the degree of representativeness of GC stability was considered. The inventors of the present invention classified miniClassifier subsets according to the six GC signatures, i.e., gastric signature, mesenchymal signature, proliferative signature, immune signature, and intestinal signature, and selected candidate genes in the subtype-specific and cohort-conserved modules. The candidates were additionally filtered by i) subtype discriminant scores (PAM analysis) and ii) intramodular connectivity (WGCNA analysis). Probe stability was evaluated based on a platform (microarray and qPCR) and the independency of a sampling method (fresh-frozen and FFPE specimens). Finally, a miniClassifier-26 qPCR probe set was obtained by reducing genes by a priori biological knowledge in cancer biology. In addition, it was confirmed that the selected miniClassifier-26 probe set was not affected by the possible spatial heterogeneity of the FFPE specimens (coefficient of variance: 5%).

A miniClassifier-26 probe set was established using the Training set II (n=1259, Merged1259, obtained on multiple platforms from fresh-frozen samples) (see FIG. 8). The GC subtypes classified using the miniClassifier-26 probe set were highly associated with prognosis in survival analysis (LR test, P=2.48e-09) (see FIG. 8D). Similar to subtypes classified by Classifier-PAM932, the INF subtype exhibited the best prognosis (the five-year survival rate of 67.3%, 95% CI: 61.3-73.9%), and the MXD subtype (the five-year survival rate of 45.0%, 95% CI: 36.5-55.4%) and the MSC subtype (the five-year survival rate of 33.0%, 95% CI: 27.3-40.0%) exhibited the worst prognosis. The consistency of trends in the survival curves of the GC subtypes (see FIG. 8D) was confirmed also in qPCR325 test sets (see FIG. 8E, P=0.000534). The five-year survival rate of the INF subtype with the best prognosis was 78.5% (95% CI: 69.4-88.8%), and the five-year survival rates of the MXD and MSC subtypes with the worst prognosis were 54.6% (95% CI: 41.7-71.4%) and 57.5% (95% CI: 48.4-68.2%), respectively.

The five confirmed gastric cancer molecular subtypes were identified in personal and well-known data sets (GSE13861p, GSE15459, TCGA, and SGE62254).

As illustrated in FIG. 8, the inflammatory molecular subtype is associated with immune signature, the intestinal molecular subtype is associated with the high expression of intestinal epithelial differentiation genes, and the gastric molecular subtype is associated with the high expression of gastric mucosa-specific genes. The mixed-stromal molecular subtype exhibits heterogeneous transit-amplifying characteristics, and the mesenchymal molecular subtype is associated with EMT and mesenchymal characteristics.

Table 3 describes the target gene expression patterns of FIG. 8A in terms of scores ($d'_{ik}$). In the scores ($d'_{ik}$) as provided in Table 3, positive numbers denote high gene expression, negative numbers denote low gene expression, and 0 denotes no change in gene expression. Thus, the more positive the score, the higher the gene expression, and the more negative the score, the lower the gene expression.

TABLE 3

Molecular subtype classification reference table, $d'_{ik}$

| signature | Gene name | Molecular subtype | | | | |
| --- | --- | --- | --- | --- | --- | --- |
| | | GST | MSC | INF | MXD | INT |
| Gastric | TFF1 | 5.79042 | −0.77487 | −1.60336 | −3.74536 | 1.405637 |
| | TFF2 | 7.261728 | 0.125744 | −1.90636 | −4.92322 | 0.282166 |
| | VSIG1 | 5.43225 | 0.676749 | 0 | −3.77475 | −1.73528 |
| Mesenchymal | CNN1 | −0.38563 | 6.066372 | −2.73467 | −0.2289 | −3.78749 |
| | NEXN | −0.31125 | 5.523202 | −1.84385 | 0.061904 | −4.42691 |
| | SCRG1 | 0.035119 | 6.184015 | −2.58117 | 0.734977 | −5.35065 |
| | SORBS1 | 0 | 4.114709 | −2.22306 | 0 | −2.45196 |
| | SPARCL1 | 0 | 5.482394 | −2.1124 | −0.47046 | −3.84298 |
| Proliferative | AURKA | 0.06389 | −1.39487 | 0.516858 | 0.548502 | 0.460776 |
| | BUB1 | 0.007791 | −2.98824 | 1.132822 | 0.703528 | 1.649687 |
| | CDC20 | 0.595127 | −3.58249 | 1.676981 | 0.679837 | 1.436201 |
| | CEP55 | 0.471205 | −2.79214 | 1.807234 | 0.623274 | 0.512529 |
| | PTTG1 | 0 | −2.97661 | 1.877958 | 0.617296 | 1.081789 |
| | UBE2C | 0 | −3.15876 | 1.383331 | 0.71818 | 1.729608 |
| Immune | WARS | 0.374598 | −0.90165 | 2.998455 | −0.29396 | −1.76155 |
| | CD8A | 0.476849 | 1.302821 | 2.354663 | −0.13816 | −4.13092 |
| | NKG7 | 0.489444 | 0.701763 | 2.919867 | −0.34839 | −3.82988 |
| | GBP1 | −0.27312 | 0.323953 | 3.151314 | 0.114002 | −3.44722 |
| | GBP5 | −0.09979 | −0.20596 | 4.17765 | −0.33953 | −3.22494 |
| | GZMB | 0.700318 | −0.7865 | 3.864089 | 0 | −3.25334 |
| Intestinal | CDH17 | 0.480373 | −0.47566 | −5.93442 | 2.960223 | 3.769466 |
| | CDX1 | −0.32734 | −0.7605 | −5.00726 | 3.781794 | 3.283526 |
| | MYO1A | 1.215205 | −1.24902 | −2.97939 | 1.264486 | 2.561301 |

TABLE 3-continued

Molecular subtype classification reference table, $d'_{ik}$

| signature | Gene name | Molecular subtype | | | | |
| --- | --- | --- | --- | --- | --- | --- |
| | | GST | MSC | INF | MXD | INT |
| Stem-like | ANTXR1 | −0.2461 | 2.607131 | −1.6872 | 0.768521 | −1.73629 |
| | SFRP4 | −1.30339 | 3.262537 | −1.03758 | 1.096524 | −2.65513 |
| | VCAN | −0.18046 | 1.739665 | −0.52306 | 0.569731 | −1.74826 |

Score values (SVs) are calculated by applying the scores ($d'_{ik}$) to Equation 2 below, and GC may be classified into an intestinal molecular subtype, an inflammatory molecular subtype, a mesenchymal molecular subtype, a mixed-stromal molecular subtype, and a gastric molecular subtype according to the SVs:

$$SV \text{ (Score Value)} = \frac{1}{t} \sum_{i \in SN_\theta} d'_{ik} \qquad \text{[Equation 2]}$$

wherein SV is an expression mean of each signature in the clusters obtained from NMF-based clustering, t is the number of genes (i) belonging to each signature, $SN_\theta$ is signature (θ=6), k denotes the number of clusters, which is an integer of 2 to 7, and ik denotes a score based on a distance between the median of total gene and a mean of each cluster.

Figure 10:
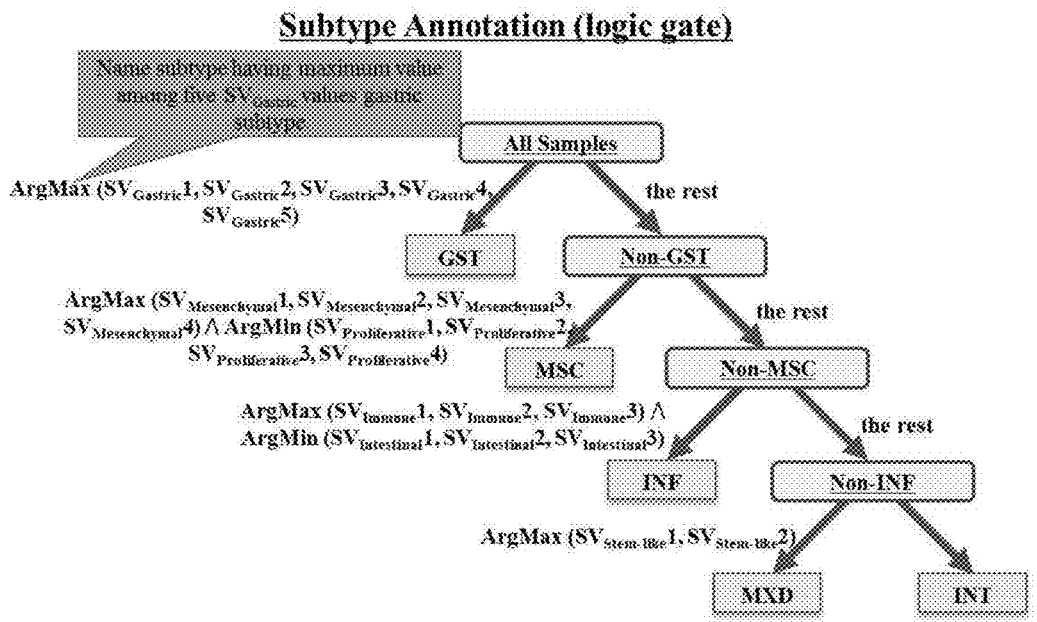
FIG. 10 illustrates a method of naming five clusters, which were obtained through NMF clustering, subtypes.

FIG. 10 illustrates a method of naming five clusters subtypes, wherein a cluster in which the SV of the gastric signature is a maximum value is determined as a gastric molecular subtype; among the remaining four clusters, a cluster in which the SV of the mesenchymal signature is a maximum value and the SV of the proliferative signature is a minimum value is determined as a mesenchymal molecular subtype; among the remaining three clusters, a cluster in which the SV of the immune signature is a maximum value and the SV of the intestinal signature is a minimum value is determined as an inflammatory molecular subtype; among the remaining two clusters, a cluster in which the SV of the stem-like signature is a maximum value is determined as a mixed-stromal molecular subtype; and the last remaining cluster is determined as an intestinal molecular subtype.

The score ($d'_{ik}$) provided in Table 3 may be corrected using a critical value for t-statistics of the (ith) gene, and the $d'_{ik}$ values may be calculated according to Equations 3 and 4 below to establish molecular subtyping standards:

$$d'_{ik} = \text{sign}(d_{ik})(|d_{ik}| - \Delta)_+ \qquad \text{[Equation 3]}$$

wherein most mean values $$\left( \bar{x}_{ik} = \sum_{j \in C_k} \frac{x_{ij}}{n_k} \right)$$

of the (ith) gene in molecular subtype (k) are noises and may approximate to a total mean $$\left( \bar{x}_i = \sum_{j=1}^{n} \frac{x_{ij}}{n} \right)$$

of the same gene types (i), and thus correction is made using a critical value (Δ) so that genes whose $d_{ik}$ values converge to 0 can be excluded. Accordingly, a reliable mean of the (ith) gene belonging to molecular subtype (k) may be calculated. The $d_{ik}$ value of Equation 3 may be calculated by Equation 4 below:

$$d_{ik} = \frac{\bar{x}_{ik} - \bar{x}_i}{m_k(s_i + s_0)}, \qquad \text{[Equation 4]}$$

$$s_i^2 = \frac{1}{n-k} \sum_{k=1}^{5} \sum_{j \in C_k} (x_{ij} - \bar{x}_{ik})^2$$

wherein $$\bar{x}_{ik} = \sum_{j \in C_k} \frac{x_{ij}}{n_k}$$

is an expression mean of the (ith) gene in molecular subtype (k), $$\bar{x}_i = \sum_{j=1}^{n} \frac{x_{ij}}{n}$$

is a total mean of the same (ith) gene, $m_k$ denotes a degree of freedom $$\left( m_k = \sqrt{\frac{1}{n_k} + \frac{1}{n}} \right)$$

for correcting a standard error of $\bar{x}_{ik} - \bar{x}_i$, $s_i$ denotes a standard deviation of the entire sample of the (i) gene belonging to molecular subtype (k), and $s_0$ denotes a median of $s_i$.

Table 3 is a molecular subtype classification reference table, wherein red color denotes maximum values and blue color denotes minimum values, and this table was made based on the $d'_{ik}$ calculated according to Equations 3 and 4 from the scores ($d'_{ik}$) of 26 target genes from 325 samples.

To confirm the molecular subtype of a test sample, the values calculated by Equations 3 and 4 above for the expression values of the target gene group of the test sample may be applied to Equation 5 below and the molecular subtype classification reference table may be used for the score ($d'_{ik}$) of Table 3, thereby determining the molecular subtype (k) of a test sample (x*):

$$\delta_k(x^*) = \sum_{i=1}^{p} \frac{(x_i^* - \bar{x}'_{ik})^2}{(s_1 - s_0)} - 2\log\pi_k, \min_k \delta_k(x^*)$$

[Equation 5]

$$\sum_{k=1}^{K} \pi_k = 1, \pi_k = \frac{1}{K};$$

$\pi_k$ is prior probability of molecular subtype (k) wherein the test sample ($x^*_i$) refers to a value obtained by median-centering the Cq values of 26 target genes with the Cq values of 26 target genes of test set II of 325 samples, $\delta_k(x^*)$ is a discriminant score for the molecular subtype "k" of the test sample ($x^*$) wherein classification is performed by selecting a molecular subtype (k) of the test sample which has the smallest discriminant score. Table 4 shows a consistency rate and error rate of the determination of molecular subtypes for 325 samples in accordance with $\delta_k(x^*)$.

TABLE 4

Consistency rate and error rate of NMF and discriminant score according to molecular subtype, n = 325

| Discriminant score | NMF | | | | | Error rate (%) |
|---|---|---|---|---|---|---|
| | Intestinal | Inflammatory | Mesenchymal | Mixed-stromal | Gastric | |
| Intestinal | 38 | 0 | 0 | 0 | 0 | 0% |
| Inflammatory | 0 | 46 | 0 | 0 | 0 | 0% |
| Mesenchymal | 0 | 3 | 84 | 0 | 2 | 5.60% |
| Mixed-stromal | 31 | 20 | 13 | 44 | 1 | 59.60% |
| Gastric | 6 | 2 | 0 | 0 | 35 | 19.60% |
| Total Error rate | | | | | | 16.96% |

The present invention can be applied to the field of gastric cancer prognosis prediction.

What is claimed is:

1. A method of predicting a prognosis of stage II and III gastric cancer, the method comprising:
   in a sufficiently statistically significant number of reference samples and biological samples obtained from stage II or III advanced gastric cancer patients,
   measuring mRNA expression levels of a target gene group and a reference gene group, the target gene group including: a gastric signature consisting of TFF1, TFF2, and VSIG1; a mesenchymal signature consisting of CNN1, NEXN, SCRG1, SORBS1, and SPARCL1; a proliferative signature consisting of AURKA, BUB1, CDC20, CEP55, PTTG1, and UBE2C; an immune signature consisting of CD8A, GBP1, GBP5, GZMB, NKG7, and WARS; a stem-like signature consisting of ANTXR1, SFRP4, and VCAN; and an intestinal signature consisting of CDH17, CDX1, and MYO1A, and the reference gene group including ACTB, ATP5E, GPX1, UBB, and HPRT1;
   wherein the agents for measuring an mRNA expression level of the target gene group and the reference gene group include a set of primers set forth in SEQ ID NOs: 1 to 62 and probes set forth in SEQ ID NOs: 63-93:

calculating ΔCq values of the target gene groups of the reference samples and the biological samples according to Equation 1 below and inputting the ΔCq values to a computer program; and performing non-negative matrix factorization (NMF) and NMF-based clustering on the values input to the computer program to be classified into a plurality of clusters, calculating a score value (SV) by applying a score ($d'_{ik}$) of a target gene group in each cluster to Equation 2 below, classifying the clusters into an intestinal molecular subtype, an inflammatory molecular subtype, a mesenchymal molecular subtype, a mixed-stromal molecular subtype, and a gastric molecular subtype, and predicting a prognosis of a molecular subtype to which the biological samples belong by analyzing the prognosis in terms of overall survival, wherein the molecular subtypes of gastric cancer are classified such that a cluster in which the SV of the gastric signature is a maximum value is determined as a gastric molecular subtype; among clusters except for the cluster determined as the gastric molecular subtype, a cluster in which the SV of the mesenchymal signature is a maximum value and the SV of the proliferative signature is a minimum value is determined as a mesenchymal molecular subtype; among clusters except for the cluster determined as the gastric molecular subtype and the cluster determined as the mesenchymal molecular subtype, a cluster in which the SV of the immune signature is a maximum value and the SV of the intestinal signature is a minimum value is determined as an inflammatory molecular subtype; among clusters except for the cluster determined as the gastric molecular subtype, the cluster determined as the mesenchymal molecular subtype, and the cluster determined as the inflammatory molecular subtype, a cluster in which the SV of the stem-like signature is a maximum value is determined as a mixed-stromal molecular subtype; and a last remaining cluster is determined as an intestinal molecular subtype, and a prognosis of gastric cancer is predicted, in terms of overall survival, such that the inflammatory molecular subtype is predicted as a good prognosis group; the intestinal molecular subtype and the gastric molecular subtype are predicted as intermediate prognosis group; and the mixed-stromal molecular subtype and the mesenchymal molecular subtype are predicted as bad prognosis group:

$$\Delta Cq = (Cq \text{ value of target gene}) - (Cq \text{ mean of reference gene group}) \quad \text{[Equation 1]}$$

wherein the Cq mean of reference gene group denotes a mean of Cq values of the reference gene group including ACTB, ATP5E, GPX1, UBB, and HPRT1, $$SV \text{ (Score Value)} = \frac{1}{t} \sum_{i \in SN_\theta} d'_{ik} \quad \text{[Equation 2]}$$

wherein SV is an expression mean of each signature in the clusters obtained from NMF-based clustering, t is the number of genes (i) belonging to each signature, $SN_\theta$ is signature (θ=6), k denotes the number of clusters, which is an integer of 2 to 7, and $d'_{ik}$ denotes a score based on a distance between a median of total gene and a mean of each cluster and is obtained according to Equation 3 below:

$$d'_{ik} = \text{sign}(d_{ik})(|d_{ik}| - \Delta)_+ \quad \text{[Equation 3]}$$

wherein a critical value (Δ) is set at 0.1 so that genes with no specificity according to molecular subtype are converged to 0, $\text{sign}(d_{ik})$ denotes a sign of $d_{ik}$, and $d_{ik}$ is obtained according to Equation 4 below;

$$d_{ik} = \frac{\bar{x}_{ik} - \bar{x}_i}{m_k(s_i + s_0)}, \quad \text{[Equation 4]}$$

$$s_i^2 = \frac{1}{n-k} \sum_{k=1}^{5} \sum_{j \in C_k} (x_{ij} - \bar{x}_{ik})^2$$

wherein $$\bar{x}_{ik} = \sum_{j \in C_k} \frac{x_{ij}}{n_k}$$

is an expression mean of the (ith) gene in molecular subtype (k), $$\bar{x}_i = \sum_{j=1}^{n} \frac{x_{ij}}{n}$$

is a total mean of the same (ith) gene, $m_k$ denotes a degree of freedom $$\left( m_k = \sqrt{\frac{1}{n_k} + \frac{1}{n}} \right)$$

for correcting a standard error of $\bar{x}_{ik} - \bar{x}_i$, $s_i$ denotes a standard deviation of the entire sample of the (i) gene belonging to molecular subtype (k), and $s_0$ denotes a median of $s_i$.

2. The method of claim 1, wherein the number of samples sufficient to exhibit a statistical significance ranges from 300 to 10,000.

3. The method of claim 1, wherein the biological sample is selected from the group consisting of fresh tumor tissue, fresh-frozen tumor tissue, formalin-fixed paraffin-embedded tumor tissue, a fine needle aspirate, ascites, a tube washing solution, and a pleural fluid.

4. The method of claim 1, wherein the measuring of an mRNA expression level of the target gene group or the reference gene group is performed by quantitative real-time polymerase chain reaction (qPCR).

* * * * *

SEQUENCE LISTING

```
<160> NUMBER OF SEQ ID NOS: 93

<210> SEQ ID NO 1
<211> LENGTH: 20
<212> TYPE: DNA
<213> ORGANISM: Artificial Sequence
<220> FEATURE:
<223> OTHER INFORMATION: TFF1 forward primer

<400> SEQUENCE: 1
aaataagggc tgctgtttcg                                                   20

<210> SEQ ID NO 2
<211> LENGTH: 20
<212> TYPE: DNA
<213> ORGANISM: Artificial Sequence
<220> FEATURE:
<223> OTHER INFORMATION: TFF1 reverse primer

<400> SEQUENCE: 2
gggacgtcga tggtattagg                                                   20

<210> SEQ ID NO 3
<211> LENGTH: 19
<212> TYPE: DNA
<213> ORGANISM: Artificial Sequence
<220> FEATURE:
<223> OTHER INFORMATION: TFF2 forward primer

<400> SEQUENCE: 3
ccctcccaaa gcaagagtc                                                    19
```

```
<210> SEQ ID NO 4
<211> LENGTH: 20
<212> TYPE: DNA
<213> ORGANISM: Artificial Sequence
<220> FEATURE:
<223> OTHER INFORMATION: TFF2 reverse primer

<400> SEQUENCE: 4
gggtagccac agtttcttcg                                              20

<210> SEQ ID NO 5
<211> LENGTH: 20
<212> TYPE: DNA
<213> ORGANISM: Artificial Sequence
<220> FEATURE:
<223> OTHER INFORMATION: VSIG1 forward primer

<400> SEQUENCE: 5
catcgtgcca gtgaaagaaa                                              20

<210> SEQ ID NO 6
<211> LENGTH: 21
<212> TYPE: DNA
<213> ORGANISM: Artificial Sequence
<220> FEATURE:
<223> OTHER INFORMATION: VSIG1 reverse primer

<400> SEQUENCE: 6
tgtcagattt ccaatgacca a                                            21

<210> SEQ ID NO 7
<211> LENGTH: 19
<212> TYPE: DNA
<213> ORGANISM: Artificial Sequence
<220> FEATURE:
<223> OTHER INFORMATION: CNN1 forward primer

<400> SEQUENCE: 7
agtccaccct cctggcttt                                               19

<210> SEQ ID NO 8
<211> LENGTH: 21
<212> TYPE: DNA
<213> ORGANISM: Artificial Sequence
<220> FEATURE:
<223> OTHER INFORMATION: CNN1 reverse primer

<400> SEQUENCE: 8
cttcactccc acgttcacct t                                            21

<210> SEQ ID NO 9
<211> LENGTH: 20
<212> TYPE: DNA
<213> ORGANISM: Artificial Sequence
<220> FEATURE:
<223> OTHER INFORMATION: NEXN forward primer

<400> SEQUENCE: 9
gcggcaaatg gtaaatgaag                                              20

<210> SEQ ID NO 10
<211> LENGTH: 20
<212> TYPE: DNA
<213> ORGANISM: Artificial Sequence
<220> FEATURE:
<223> OTHER INFORMATION: NEXN reverse primer
```

```
<400> SEQUENCE: 10
gggcggtacc ctttaaaaat                                              20

<210> SEQ ID NO 11
<211> LENGTH: 20
<212> TYPE: DNA
<213> ORGANISM: Artificial Sequence
<220> FEATURE:
<223> OTHER INFORMATION: SCRG1 forward primer

<400> SEQUENCE: 11
cccagtgagt gtgagcattt                                              20

<210> SEQ ID NO 12
<211> LENGTH: 20
<212> TYPE: DNA
<213> ORGANISM: Artificial Sequence
<220> FEATURE:
<223> OTHER INFORMATION: SCRG1 reverse primer

<400> SEQUENCE: 12
gcttttggcc cttttcttc                                               20

<210> SEQ ID NO 13
<211> LENGTH: 19
<212> TYPE: DNA
<213> ORGANISM: Artificial Sequence
<220> FEATURE:
<223> OTHER INFORMATION: SORBS1 forward primer

<400> SEQUENCE: 13
gctgtgatga atggcttgg                                               19

<210> SEQ ID NO 14
<211> LENGTH: 21
<212> TYPE: DNA
<213> ORGANISM: Artificial Sequence
<220> FEATURE:
<223> OTHER INFORMATION: SORBS1 reverse primer

<400> SEQUENCE: 14
cccagtgcag atttttgtag g                                            21

<210> SEQ ID NO 15
<211> LENGTH: 20
<212> TYPE: DNA
<213> ORGANISM: Artificial Sequence
<220> FEATURE:
<223> OTHER INFORMATION: SPARCL1 forward primer

<400> SEQUENCE: 15
cattccaaac caactgctga                                              20

<210> SEQ ID NO 16
<211> LENGTH: 20
<212> TYPE: DNA
<213> ORGANISM: Artificial Sequence
<220> FEATURE:
<223> OTHER INFORMATION: SPARCL1 reverse primer

<400> SEQUENCE: 16
agcttcagcc cataaactgg                                              20
```

```
<210> SEQ ID NO 17
<211> LENGTH: 20
<212> TYPE: DNA
<213> ORGANISM: Artificial Sequence
<220> FEATURE:
<223> OTHER INFORMATION: AURKA forward primer

<400> SEQUENCE: 17
gcagattttg ggtggtcagt                                               20

<210> SEQ ID NO 18
<211> LENGTH: 20
<212> TYPE: DNA
<213> ORGANISM: Artificial Sequence
<220> FEATURE:
<223> OTHER INFORMATION: AURKA reverse primer

<400> SEQUENCE: 18
gtagtccagg gtgccacaga                                               20

<210> SEQ ID NO 19
<211> LENGTH: 20
<212> TYPE: DNA
<213> ORGANISM: Artificial Sequence
<220> FEATURE:
<223> OTHER INFORMATION: BUB1 forward primer

<400> SEQUENCE: 19
ccttcaaaac caaaggagga                                               20

<210> SEQ ID NO 20
<211> LENGTH: 19
<212> TYPE: DNA
<213> ORGANISM: Artificial Sequence
<220> FEATURE:
<223> OTHER INFORMATION: BUB1 reverse primer

<400> SEQUENCE: 20
gcagcgaata ccccataca                                                19

<210> SEQ ID NO 21
<211> LENGTH: 19
<212> TYPE: DNA
<213> ORGANISM: Artificial Sequence
<220> FEATURE:
<223> OTHER INFORMATION: CDC20 forward primer

<400> SEQUENCE: 21
cttccctgcc agaccgtat                                                19

<210> SEQ ID NO 22
<211> LENGTH: 20
<212> TYPE: DNA
<213> ORGANISM: Artificial Sequence
<220> FEATURE:
<223> OTHER INFORMATION: CDC20 reverse primer

<400> SEQUENCE: 22
ccaatccaca aggttcaggt                                               20

<210> SEQ ID NO 23
<211> LENGTH: 20
<212> TYPE: DNA
<213> ORGANISM: Artificial Sequence
<220> FEATURE:
<223> OTHER INFORMATION: CEP55 forward primer
```

```
<400> SEQUENCE: 23
caagtgggaa aggaaagctg                                              20

<210> SEQ ID NO 24
<211> LENGTH: 20
<212> TYPE: DNA
<213> ORGANISM: Artificial Sequence
<220> FEATURE:
<223> OTHER INFORMATION: CEP55 reverse primer

<400> SEQUENCE: 24
ctcagcctca aggactcgaa                                              20

<210> SEQ ID NO 25
<211> LENGTH: 18
<212> TYPE: DNA
<213> ORGANISM: Artificial Sequence
<220> FEATURE:
<223> OTHER INFORMATION: PTTG1 forward primer

<400> SEQUENCE: 25
ctgaagctgg ggtctgga                                                18

<210> SEQ ID NO 26
<211> LENGTH: 22
<212> TYPE: DNA
<213> ORGANISM: Artificial Sequence
<220> FEATURE:
<223> OTHER INFORMATION: PTTG1 reverse primer

<400> SEQUENCE: 26
aacgtggtgt tgaaacttga ga                                           22

<210> SEQ ID NO 27
<211> LENGTH: 18
<212> TYPE: DNA
<213> ORGANISM: Artificial Sequence
<220> FEATURE:
<223> OTHER INFORMATION: UBE2C forward primer

<400> SEQUENCE: 27
ccctgctatc accccaac                                                18

<210> SEQ ID NO 28
<211> LENGTH: 20
<212> TYPE: DNA
<213> ORGANISM: Artificial Sequence
<220> FEATURE:
<223> OTHER INFORMATION: UBE2C reverse primer

<400> SEQUENCE: 28
gggcagacca cttttccttc                                              20

<210> SEQ ID NO 29
<211> LENGTH: 20
<212> TYPE: DNA
<213> ORGANISM: Artificial Sequence
<220> FEATURE:
<223> OTHER INFORMATION: CD8A forward primer

<400> SEQUENCE: 29
cagagctacc cgcagagttc                                              20
```

```
<210> SEQ ID NO 30
<211> LENGTH: 20
<212> TYPE: DNA
<213> ORGANISM: Artificial Sequence
<220> FEATURE:
<223> OTHER INFORMATION: CD8A reverse primer

<400> SEQUENCE: 30
aagaggttga gatggcatgg                                              20

<210> SEQ ID NO 31
<211> LENGTH: 20
<212> TYPE: DNA
<213> ORGANISM: Artificial Sequence
<220> FEATURE:
<223> OTHER INFORMATION: GBP1 forward primer

<400> SEQUENCE: 31
tagaagccag tgctcgtgaa                                              20

<210> SEQ ID NO 32
<211> LENGTH: 20
<212> TYPE: DNA
<213> ORGANISM: Artificial Sequence
<220> FEATURE:
<223> OTHER INFORMATION: GBP1 reverse primer

<400> SEQUENCE: 32
gatctctgat gccatgtcca                                              20

<210> SEQ ID NO 33
<211> LENGTH: 20
<212> TYPE: DNA
<213> ORGANISM: Artificial Sequence
<220> FEATURE:
<223> OTHER INFORMATION: GBP5 forward primer

<400> SEQUENCE: 33
ggcctgggag atgtagagaa                                              20

<210> SEQ ID NO 34
<211> LENGTH: 21
<212> TYPE: DNA
<213> ORGANISM: Artificial Sequence
<220> FEATURE:
<223> OTHER INFORMATION: GBP5 reverse primer

<400> SEQUENCE: 34
cagtaagagt gccagtgcaa a                                            21

<210> SEQ ID NO 35
<211> LENGTH: 20
<212> TYPE: DNA
<213> ORGANISM: Artificial Sequence
<220> FEATURE:
<223> OTHER INFORMATION: GZMB forward primer

<400> SEQUENCE: 35
cggtggcttc ctgatacaag                                              20

<210> SEQ ID NO 36
<211> LENGTH: 20
<212> TYPE: DNA
<213> ORGANISM: Artificial Sequence
<220> FEATURE:
<223> OTHER INFORMATION: GZMB reverse primer
```

<400> SEQUENCE: 36
ttatggagct tccccaacag                                              20

<210> SEQ ID NO 37
<211> LENGTH: 18
<212> TYPE: DNA
<213> ORGANISM: Artificial Sequence
<220> FEATURE:
<223> OTHER INFORMATION: NKG7 forward primer

<400> SEQUENCE: 37
gtccccgtcc tggctatg                                                18

<210> SEQ ID NO 38
<211> LENGTH: 21
<212> TYPE: DNA
<213> ORGANISM: Artificial Sequence
<220> FEATURE:
<223> OTHER INFORMATION: NKG7 reverse primer

<400> SEQUENCE: 38
aacgctcaaa actcatcttg c                                            21

<210> SEQ ID NO 39
<211> LENGTH: 20
<212> TYPE: DNA
<213> ORGANISM: Artificial Sequence
<220> FEATURE:
<223> OTHER INFORMATION: WARS forward primer

<400> SEQUENCE: 39
ttgtggaccc atggacagta                                              20

<210> SEQ ID NO 40
<211> LENGTH: 20
<212> TYPE: DNA
<213> ORGANISM: Artificial Sequence
<220> FEATURE:
<223> OTHER INFORMATION: WARS reverse primer

<400> SEQUENCE: 40
ccaaaccgaa caatgagctt                                              20

<210> SEQ ID NO 41
<211> LENGTH: 21
<212> TYPE: DNA
<213> ORGANISM: Artificial Sequence
<220> FEATURE:
<223> OTHER INFORMATION: ANTXR1 forward primer

<400> SEQUENCE: 41
cagttggctc acaaattcat c                                            21

<210> SEQ ID NO 42
<211> LENGTH: 19
<212> TYPE: DNA
<213> ORGANISM: Artificial Sequence
<220> FEATURE:
<223> OTHER INFORMATION: ANTXR1 reverse primer

<400> SEQUENCE: 42
ttcctcgggt ggagaaaac                                               19

```
<210> SEQ ID NO 43
<211> LENGTH: 22
<212> TYPE: DNA
<213> ORGANISM: Artificial Sequence
<220> FEATURE:
<223> OTHER INFORMATION: SFRP4 forward primer

<400> SEQUENCE: 43
ggagacttcc gacttcctta ca                                                22

<210> SEQ ID NO 44
<211> LENGTH: 20
<212> TYPE: DNA
<213> ORGANISM: Artificial Sequence
<220> FEATURE:
<223> OTHER INFORMATION: SFRP4 reverse primer

<400> SEQUENCE: 44
tggccttaca taggctgtcc                                                   20

<210> SEQ ID NO 45
<211> LENGTH: 20
<212> TYPE: DNA
<213> ORGANISM: Artificial Sequence
<220> FEATURE:
<223> OTHER INFORMATION: VCAN forward primer

<400> SEQUENCE: 45
tttgagcatg acttccgttg                                                   20

<210> SEQ ID NO 46
<211> LENGTH: 20
<212> TYPE: DNA
<213> ORGANISM: Artificial Sequence
<220> FEATURE:
<223> OTHER INFORMATION: VCAN reverse primer

<400> SEQUENCE: 46
ctgtctggct ggttgggtct                                                   20

<210> SEQ ID NO 47
<211> LENGTH: 20
<212> TYPE: DNA
<213> ORGANISM: Artificial Sequence
<220> FEATURE:
<223> OTHER INFORMATION: CDH17 forward primer

<400> SEQUENCE: 47
gcaatgtgac tgccaaggat                                                   20

<210> SEQ ID NO 48
<211> LENGTH: 20
<212> TYPE: DNA
<213> ORGANISM: Artificial Sequence
<220> FEATURE:
<223> OTHER INFORMATION: CDH17 reverse primer

<400> SEQUENCE: 48
acctcttgtg tctcccctca                                                   20

<210> SEQ ID NO 49
<211> LENGTH: 20
<212> TYPE: DNA
<213> ORGANISM: Artificial Sequence
<220> FEATURE:
<223> OTHER INFORMATION: CDX1 forward primer
```

<400> SEQUENCE: 49
agggaggaac gtggtcaact                                              20

<210> SEQ ID NO 50
<211> LENGTH: 20
<212> TYPE: DNA
<213> ORGANISM: Artificial Sequence
<220> FEATURE:
<223> OTHER INFORMATION: CDX1 reverse primer

<400> SEQUENCE: 50
tatgatgggg gcaggtagaa                                              20

<210> SEQ ID NO 51
<211> LENGTH: 20
<212> TYPE: DNA
<213> ORGANISM: Artificial Sequence
<220> FEATURE:
<223> OTHER INFORMATION: MYO1A forward primer

<400> SEQUENCE: 51
ccgcctcttt gactggatag                                              20

<210> SEQ ID NO 52
<211> LENGTH: 20
<212> TYPE: DNA
<213> ORGANISM: Artificial Sequence
<220> FEATURE:
<223> OTHER INFORMATION: MYO1A reverse primer

<400> SEQUENCE: 52
ccttcttctt ttccccgatg                                              20

<210> SEQ ID NO 53
<211> LENGTH: 20
<212> TYPE: DNA
<213> ORGANISM: Artificial Sequence
<220> FEATURE:
<223> OTHER INFORMATION: ACTB forward primer

<400> SEQUENCE: 53
tcaccctgaa gtaccccatc                                              20

<210> SEQ ID NO 54
<211> LENGTH: 20
<212> TYPE: DNA
<213> ORGANISM: Artificial Sequence
<220> FEATURE:
<223> OTHER INFORMATION: ACTB reverse primer

<400> SEQUENCE: 54
tgtggtgcca gattttctcc                                              20

<210> SEQ ID NO 55
<211> LENGTH: 20
<212> TYPE: DNA
<213> ORGANISM: Artificial Sequence
<220> FEATURE:
<223> OTHER INFORMATION: ATP5E forward primer

<400> SEQUENCE: 55
atggtggcct actggagaca                                              20

<210> SEQ ID NO 56
<211> LENGTH: 21
<212> TYPE: DNA
<213> ORGANISM: Artificial Sequence
<220> FEATURE:
<223> OTHER INFORMATION: ATP5E reverse primer

<400> SEQUENCE: 56
ctctcactgc ttttgcacag a                                          21

<210> SEQ ID NO 57
<211> LENGTH: 18
<212> TYPE: DNA
<213> ORGANISM: Artificial Sequence
<220> FEATURE:
<223> OTHER INFORMATION: GPX1 forward primer

<400> SEQUENCE: 57
cccgtgcaac cagtttgg                                              18

<210> SEQ ID NO 58
<211> LENGTH: 23
<212> TYPE: DNA
<213> ORGANISM: Artificial Sequence
<220> FEATURE:
<223> OTHER INFORMATION: GPX1 reverse primer

<400> SEQUENCE: 58
ggacgtactt gagggaattc aga                                        23

<210> SEQ ID NO 59
<211> LENGTH: 20
<212> TYPE: DNA
<213> ORGANISM: Artificial Sequence
<220> FEATURE:
<223> OTHER INFORMATION: UBB forward primer

<400> SEQUENCE: 59
tgggtgagct tgtttgtgtc                                            20

<210> SEQ ID NO 60
<211> LENGTH: 21
<212> TYPE: DNA
<213> ORGANISM: Artificial Sequence
<220> FEATURE:
<223> OTHER INFORMATION: UBB reverse primer

<400> SEQUENCE: 60
tttgacctgt tagcggatac c                                          21

<210> SEQ ID NO 61
<211> LENGTH: 21
<212> TYPE: DNA
<213> ORGANISM: Artificial Sequence
<220> FEATURE:
<223> OTHER INFORMATION: HPRT1 forward primer

<400> SEQUENCE: 61
tggtcaggca gtataatcca a                                          21

<210> SEQ ID NO 62
<211> LENGTH: 20
<212> TYPE: DNA
<213> ORGANISM: Artificial Sequence
<220> FEATURE:
<223> OTHER INFORMATION: HPRT1 reverse primer

<400> SEQUENCE: 62
cttcgtgggg tccttttcac                                              20

<210> SEQ ID NO 63
<211> LENGTH: 20
<212> TYPE: DNA
<213> ORGANISM: Artificial Sequence
<220> FEATURE:
<223> OTHER INFORMATION: TFF1 probe

<400> SEQUENCE: 63
acgacaccgt tcgtggggtc                                              20

<210> SEQ ID NO 64
<211> LENGTH: 22
<212> TYPE: DNA
<213> ORGANISM: Artificial Sequence
<220> FEATURE:
<223> OTHER INFORMATION: TFF2 probe

<400> SEQUENCE: 64
tcagtgcgtc atggaggtct ca                                           22

<210> SEQ ID NO 65
<211> LENGTH: 20
<212> TYPE: DNA
<213> ORGANISM: Artificial Sequence
<220> FEATURE:
<223> OTHER INFORMATION: VSIG1 probe

<400> SEQUENCE: 65
tcaacccaac caccgggatt                                              20

<210> SEQ ID NO 66
<211> LENGTH: 22
<212> TYPE: DNA
<213> ORGANISM: Artificial Sequence
<220> FEATURE:
<223> OTHER INFORMATION: CNN1 probe

<400> SEQUENCE: 66
cctttcgtct tcgccatgct gg                                           22

<210> SEQ ID NO 67
<211> LENGTH: 24
<212> TYPE: DNA
<213> ORGANISM: Artificial Sequence
<220> FEATURE:
<223> OTHER INFORMATION: NEXN probe

<400> SEQUENCE: 67
tgaggaaaac caagacacag caaa                                         24

<210> SEQ ID NO 68
<211> LENGTH: 22
<212> TYPE: DNA
<213> ORGANISM: Artificial Sequence
<220> FEATURE:
<223> OTHER INFORMATION: SCRG1 probe

<400> SEQUENCE: 68
tggtcttggc agaggatgct tc                                           22

```
<210> SEQ ID NO 69
<211> LENGTH: 20
<212> TYPE: DNA
<213> ORGANISM: Artificial Sequence
<220> FEATURE:
<223> OTHER INFORMATION: SORBS1 probe

<400> SEQUENCE: 69
ttgtcttgcc cattgctgcc                                              20

<210> SEQ ID NO 70
<211> LENGTH: 22
<212> TYPE: DNA
<213> ORGANISM: Artificial Sequence
<220> FEATURE:
<223> OTHER INFORMATION: SPARCL1 probe

<400> SEQUENCE: 70
cggtagcacc tgacaacact gc                                           22

<210> SEQ ID NO 71
<211> LENGTH: 21
<212> TYPE: DNA
<213> ORGANISM: Artificial Sequence
<220> FEATURE:
<223> OTHER INFORMATION: AURKA probe

<400> SEQUENCE: 71
ctccatcttc caggaggacc a                                            21

<210> SEQ ID NO 72
<211> LENGTH: 24
<212> TYPE: DNA
<213> ORGANISM: Artificial Sequence
<220> FEATURE:
<223> OTHER INFORMATION: BUB1 probe

<400> SEQUENCE: 72
ccaaaaactc ttcagcatga ggca                                         24

<210> SEQ ID NO 73
<211> LENGTH: 20
<212> TYPE: DNA
<213> ORGANISM: Artificial Sequence
<220> FEATURE:
<223> OTHER INFORMATION: CDC20 probe

<400> SEQUENCE: 73
cctggatgcg cctgaaatcc                                              20

<210> SEQ ID NO 74
<211> LENGTH: 25
<212> TYPE: DNA
<213> ORGANISM: Artificial Sequence
<220> FEATURE:
<223> OTHER INFORMATION: CEP55 probe

<400> SEQUENCE: 74
ttttctccaa aagtctgtgt ctctc                                        25

<210> SEQ ID NO 75
<211> LENGTH: 25
<212> TYPE: DNA
<213> ORGANISM: Artificial Sequence
<220> FEATURE:
<223> OTHER INFORMATION: PTTG1 probe
```

```
<400> SEQUENCE: 75
ccttcaatca aagccttaga tggga                                        25

<210> SEQ ID NO 76
<211> LENGTH: 23
<212> TYPE: DNA
<213> ORGANISM: Artificial Sequence
<220> FEATURE:
<223> OTHER INFORMATION: UBE2C probe

<400> SEQUENCE: 76
cacccagggt aacatatgcc tgg                                          23

<210> SEQ ID NO 77
<211> LENGTH: 23
<212> TYPE: DNA
<213> ORGANISM: Artificial Sequence
<220> FEATURE:
<223> OTHER INFORMATION: CD8A probe

<400> SEQUENCE: 77
tgcctccagc tctctcagca tga                                          23

<210> SEQ ID NO 78
<211> LENGTH: 27
<212> TYPE: DNA
<213> ORGANISM: Artificial Sequence
<220> FEATURE:
<223> OTHER INFORMATION: GBP1 probe

<400> SEQUENCE: 78
agaaaaagaa cagacaaggg aacagcc                                      27

<210> SEQ ID NO 79
<211> LENGTH: 26
<212> TYPE: DNA
<213> ORGANISM: Artificial Sequence
<220> FEATURE:
<223> OTHER INFORMATION: GBP5 probe

<400> SEQUENCE: 79
tctggatatc attcttgttg tcagcc                                       26

<210> SEQ ID NO 80
<211> LENGTH: 21
<212> TYPE: DNA
<213> ORGANISM: Artificial Sequence
<220> FEATURE:
<223> OTHER INFORMATION: GZMB probe

<400> SEQUENCE: 80
cgacttcgtg ctgacagctg c                                            21

<210> SEQ ID NO 81
<211> LENGTH: 21
<212> TYPE: DNA
<213> ORGANISM: Artificial Sequence
<220> FEATURE:
<223> OTHER INFORMATION: NKG7 probe

<400> SEQUENCE: 81
cgctcttgcc ttctgctcac a                                            21
```

```
<210> SEQ ID NO 82
<211> LENGTH: 22
<212> TYPE: DNA
<213> ORGANISM: Artificial Sequence
<220> FEATURE:
<223> OTHER INFORMATION: WARS probe

<400> SEQUENCE: 82
tgccttttgc actgcttgtc tg                                              22

<210> SEQ ID NO 83
<211> LENGTH: 23
<212> TYPE: DNA
<213> ORGANISM: Artificial Sequence
<220> FEATURE:
<223> OTHER INFORMATION: ANTXR1 probe

<400> SEQUENCE: 83
aaaggacatt ctcaactgtg ggc                                             23

<210> SEQ ID NO 84
<211> LENGTH: 20
<212> TYPE: DNA
<213> ORGANISM: Artificial Sequence
<220> FEATURE:
<223> OTHER INFORMATION: SFRP4 probe

<400> SEQUENCE: 84
aggcaatgcc cagcctcatc                                                 20

<210> SEQ ID NO 85
<211> LENGTH: 21
<212> TYPE: DNA
<213> ORGANISM: Artificial Sequence
<220> FEATURE:
<223> OTHER INFORMATION: VCAN probe

<400> SEQUENCE: 85
tggcagcaca ctgcaatacg a                                               21

<210> SEQ ID NO 86
<211> LENGTH: 21
<212> TYPE: DNA
<213> ORGANISM: Artificial Sequence
<220> FEATURE:
<223> OTHER INFORMATION: CDH17 probe

<400> SEQUENCE: 86
ccagaaggtc tggacataag c                                               21

<210> SEQ ID NO 87
<211> LENGTH: 20
<212> TYPE: DNA
<213> ORGANISM: Artificial Sequence
<220> FEATURE:
<223> OTHER INFORMATION: CDX1 probe

<400> SEQUENCE: 87
tgcctcttcc tgcagcctca                                                 20

<210> SEQ ID NO 88
<211> LENGTH: 25
<212> TYPE: DNA
<213> ORGANISM: Artificial Sequence
<220> FEATURE:
<223> OTHER INFORMATION: MYO1A probe
```

```
<400> SEQUENCE: 88
cccaccttga tgctctcatt gattc                                          25

<210> SEQ ID NO 89
<211> LENGTH: 20
<212> TYPE: DNA
<213> ORGANISM: Artificial Sequence
<220> FEATURE:
<223> OTHER INFORMATION: ACTB probe

<400> SEQUENCE: 89
cggcatcgtc accaactggg                                                20

<210> SEQ ID NO 90
<211> LENGTH: 27
<212> TYPE: DNA
<213> ORGANISM: Artificial Sequence
<220> FEATURE:
<223> OTHER INFORMATION: ATP5E probe

<400> SEQUENCE: 90
tggactcagc tacatccgat actccca                                        27

<210> SEQ ID NO 91
<211> LENGTH: 27
<212> TYPE: DNA
<213> ORGANISM: Artificial Sequence
<220> FEATURE:
<223> OTHER INFORMATION: GPX1 probe

<400> SEQUENCE: 91
ctcttcgttc ttggcgttct cctgatg                                        27

<210> SEQ ID NO 92
<211> LENGTH: 20
<212> TYPE: DNA
<213> ORGANISM: Artificial Sequence
<220> FEATURE:
<223> OTHER INFORMATION: UBB probe

<400> SEQUENCE: 92
caccaaccac gtccacccac                                                20

<210> SEQ ID NO 93
<211> LENGTH: 21
<212> TYPE: DNA
<213> ORGANISM: Artificial Sequence
<220> FEATURE:
<223> OTHER INFORMATION: HPRT1 probe

<400> SEQUENCE: 93
tgcaagcttg cgaccttgac c                                              21
```